US012672934B2

(12) United States Patent
Tripathi

(10) Patent No.: US 12,672,934 B2
(45) Date of Patent: *Jul. 7, 2026

(54) REAL-TIME SURGICAL REFERENCE INDICIUM APPARATUS AND METHODS FOR INTRAOCULAR LENS IMPLANTATION

(71) Applicant: ALCON INC., Fribourg (CH)

(72) Inventor: Ashok Burton Tripathi, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/085,275

(22) Filed: Mar. 20, 2025

(65) Prior Publication Data

US 2025/0213323 A1 Jul. 3, 2025

Related U.S. Application Data

(60) Continuation of application No. 18/339,785, filed on Jun. 22, 2023, now Pat. No. 12,279,917, which is a continuation of application No. 17/235,969, filed on Apr. 21, 2021, now Pat. No. 11,723,746, which is a continuation of application No. 14/929,801, filed on Nov. 2, 2015, now Pat. No. 11,039,901, which is a division of application No. 12/390,388, filed on Feb. 20, 2009, now Pat. No. 9,173,717.

(51) Int. Cl.
| | |
|---|---|
| A61B 90/00 | (2016.01) |
| A61B 34/10 | (2016.01) |
| A61F 2/16 | (2006.01) |

(52) U.S. Cl.
CPC ................ *A61B 90/37* (2016.02); *A61F 2/16* (2013.01); *A61B 2034/107* (2016.02); *A61B 2090/365* (2016.02)

(58) Field of Classification Search
None
See application file for complete search history.

*Primary Examiner* — Michael J Carey
*Assistant Examiner* — Marjan Saboktakin

(57) ABSTRACT

A system, method, and apparatus for performing intraocular lens implantation using real-time surgical reference indicium are disclosed. An example method includes recording a patient specific pre-operative still image of an eye prior to cyclorotation of the eye when a patient lies down for surgery and generating at least one real-time multidimensional visualization of at least a portion of the eye for display. The method further includes using the patient specific pre-operative still image to at least produce at least one virtual surgical reference indicium including an ocular natural vertical axis of the eye and align the at least one virtual surgical reference indicium to the eye in conjunction with the real-time multidimensional visualization of at least a portion of the eye. The patient specific pre-operative still image is captured under a dilation condition selected from the group consisting of natural dilation, chemical dilation, and no dilation.

20 Claims, 11 Drawing Sheets

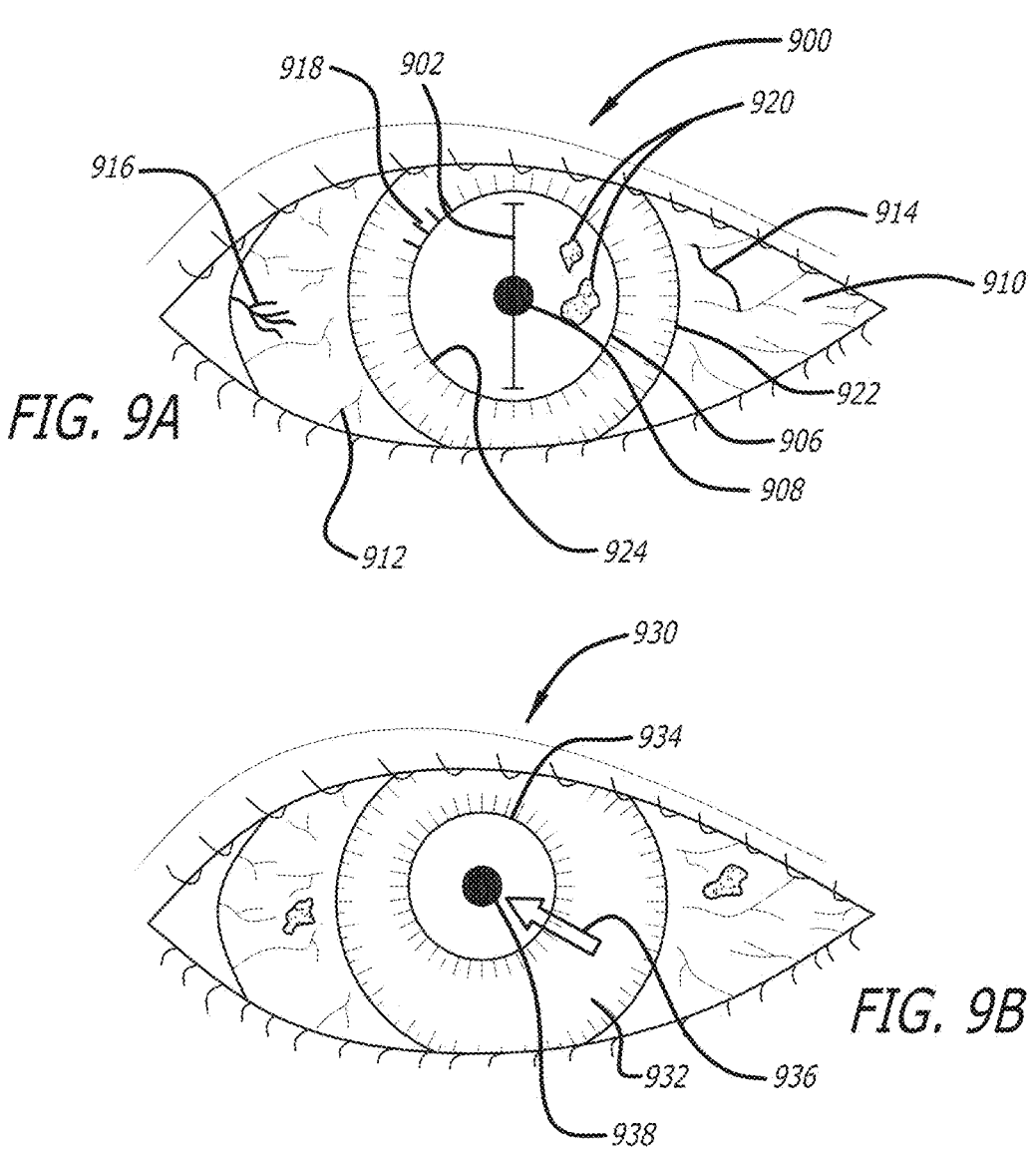
*FIG. 9A*
*FIG. 9B*
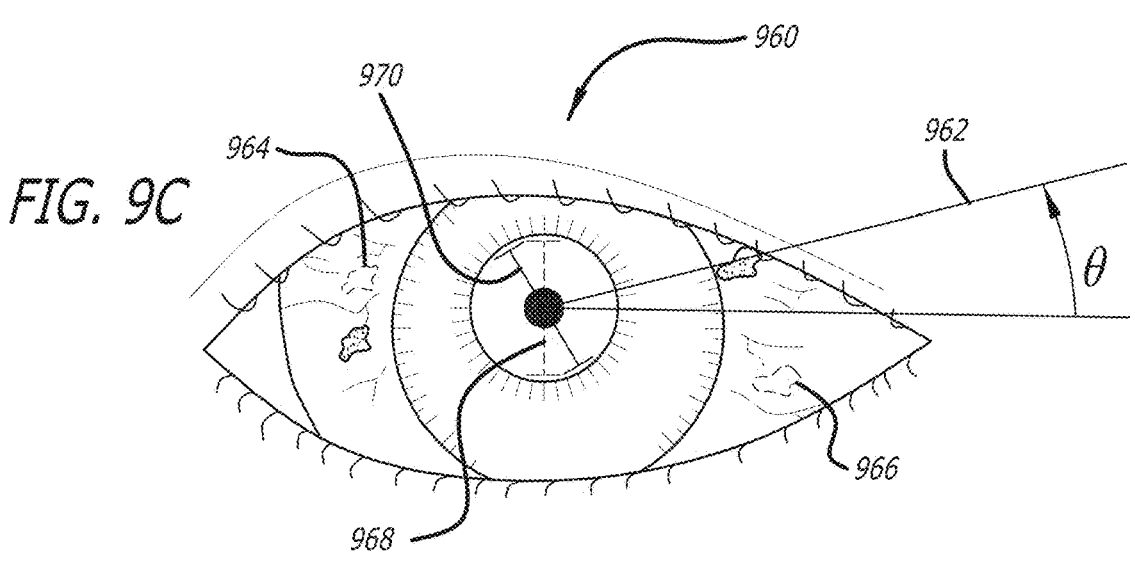
*FIG. 9C*

REAL-TIME SURGICAL REFERENCE INDICIUM APPARATUS AND METHODS FOR INTRAOCULAR LENS IMPLANTATION

PRIORITY CLAIM

This application is a continuation of U.S. patent application Ser. No. 18/339,785, filed Jun. 22, 2023, which is a continuation of U.S. Pat. No. 11,723,746 (Ser. No. 17/235, 969, filed Apr. 21, 2021), which is a continuation application of U.S. Pat. No. 11,039,901 (Ser. No. 14/929,801, filed Nov. 2, 2015), which is a divisional application of U.S. Pat. No. 9,173,717 (Ser. No. 12/390,388, filed Feb. 20, 2009). The entire contents of each of the above-listed references is hereby incorporated by reference.

TECHNICAL FIELD

The present description generally relates to the field of ocular surgery, and more particularly to ocular surgical procedures utilizing visual imaging systems including open or unmagnified surgery and micro-surgery utilizing visual imaging systems with magnification such as implantation of intraocular lenses.

BACKGROUND

Ocular surgery, whether reconstructive, cosmetic, palliative, or otherwise, is highly patient specific. Even though most surgery patients have the same basic ocular architecture, every eye has its own set of specific features and dimensions that in certain cases may be significantly different from those of expected norms. As a result, surgeons must rely upon their individual experience and skills to adapt whatever surgical techniques they are practicing to the individual requirements as determined by each patient's unique ocular structural features and dimensions.

To date, this individualized surgical adaptation has been accomplished essentially through freehand and best guess techniques based upon a pre-surgery examination and evaluation of the individual patient's ocular region. This examination may include preliminary measurements as well as the surgeon making reference markings directly on the patient's ocular tissues with a pen or other form of dye or ink marking. Then, after the patient has been prepared and placed in position for surgery, typically in a supine or prone position as opposed to the often vertical positioning of the patient during the pre-surgery examinations, the surgeon adapts the placement and configuration of the initial surgical incisions to the actual physical dimensions and circumstances found in the patient as the surgical procedure progresses. As a result, many initial measurements or reference markings on the patient's ocular tissues are at best a general guide as to where to begin the procedure and have limited accuracy and influence on subsequent aspects of the procedure or on the overall outcome of the surgery.

Further complicating matters, ocular tissues are not conducive to pre-surgery reference markings or measurements. This is particularly true because most ocular tissues have wet surfaces and internal physical structures that cannot be accessed for direct measurement or marking prior to surgery. Additionally, pre-surgical rinsing, sterilization, or drug administration to the ocular tissues may dissolve, alter or even remove reference markings prior to the initiation of surgery. Similarly, subsequent wiping and contact with fluids, including the patient's body fluids, during the surgical procedure may remove or distort any remaining reference markings. As a result, even the most accurate surgical reference markings may lose any practical effectiveness beyond the initial stages of the surgical procedure.

As such, there is a continuing need for effective surgical reference indicia properly aligned with a particular axis, particularly when proper alignment of pre-surgical data is pivotal to satisfactory patient outcome. For instance, proper alignment of pre-surgical data, particularly the true vertical axis of an eye, with the ocular surgery is highly advantageous with intraocular lens (IOL) implantation and orientation of the IOL within the posterior chamber of the eye.

The implantation of an IOL is a highly sophisticated surgical procedure that, in the past, has been performed based on partially accurate or even inaccurate visual measurements and estimated alignment with the vertical or horizontal axis of a patient's eye. Past procedures have commonly relied on the measurement of an eye's vertical or horizontal axis prior to surgery and the subsequent inaccurate translation of that measurement to the IOL implantation procedure where the positioning of the measured axis of the eye may have changed. As a result, it is not uncommon for the IOL placement to be improperly aligned with the true vertical axis of the eye, resulting in such side effects as poor visual acuity, double vision, and halos under low ambient light conditions.

Accordingly, in spite of the ongoing development and the growing sophistication of contemporary ocular surgery, there is a continuing need for the provision of effective surgical reference indicia including information about or which track a patient's natural vertical axis or other important axis of orientation.

SUMMARY

The apparatus and methods described herein address the long-felt need for functional, useful, and effective ocular surgery reference markings, or indicia, including at least one natural patient vertical. Further, provided are apparatus and associated methods for the generation of at least one accurate and effective, real-time, virtual surgical reference indicium including at least one natural patient vertical in conjunction with one or more real-time, multidimensional visualizations of a target surgical field, or at least a portion thereof, throughout a surgical procedure or any subpart thereof. In one embodiment, the multidimensional visualizations can be three dimensional (3D), stereoscopic, and high definition (HD). Moreover, the virtual surgical reference indicium, or multiple reference indicia, including natural patient vertical are placed under the direct control, adjustment, and verification of the operating surgeon or surgical team. This control enables the operating surgeon or surgical team to fine tune the virtual surgical reference indicia including natural patient vertical as desired or needed and to align and lock the reference indicium including natural patient vertical in place relative to the individual patient's target anatomy. Once so aligned, the virtual surgical reference indicia including natural patient vertical function as effective guides or references for the surgeon or surgical team throughout the duration of an entire surgical procedure or any subpart thereof.

Moreover, the apparatus and methods described herein make it possible for an operating surgeon to directly remove and reinstate at least one real-time, virtual surgical reference indicium or indicia including natural patient vertical as needed at any time throughout the duration of a surgical procedure at the control of and in response to the needs of the operating surgeon. Additionally, the apparatus and methods described herein also make it possible for the operating surgeon to replace at least one initial real-time, virtual surgical reference indicium including natural patient vertical with one or more secondary or modified real-time, virtual surgical reference indicia including natural patient vertical at an appropriate time during the surgical procedure to provide additional surgical guidance in real-time as desired or needed throughout the procedure.

Further still, the apparatus and methods described herein also make it possible for the operating surgeon to utilize multiple, different real-time, virtual surgical reference indicia or natural patient vertical sequentially or simultaneously to achieve even more control over the surgical procedure or any subpart thereof.

As an added benefit, the at least one real-time virtual surgical reference indicium including natural patient vertical can be positioned accurately at an appropriate depth within the target surgical field to accurately indicate the correct reference position on or in the tissue, tissues, or structures of interest. Further, the at least one real-time virtual surgical reference indicium including natural patient vertical can be varied within the multidimensional visualization of the target surgical field as appropriate or desired during different phases of the surgical procedure where different tissues or structures are subsequently targeted or exposed. Additionally, the color, luminosity, transparency or visual characteristics of the at least one real-time, virtual surgical reference indicium and natural patient vertical may be altered as appropriate or desired by the operating surgeon to enhance their contrast and visibility relative to the color and textures of the actual target surgical field of view and to provide notice or suggestion of impending dimensional or topographical objectives or restrictions upon the movement of a surgical instrument.

Exemplary apparatus and associated methods described herein accomplish these previously unobtainable benefits through the utilization of at least one real-time, multidimensional visualization module such as the True Vision Systems, Inc. real-time 3D HD visualization systems as disclosed and claimed in the Applicant's co-pending patent applications made of reference herein. These exemplary multidimensional visualization modules function as either retrofit devices attached to existing stereomicroscopes in place of traditional microscope binocular optics or as standalone stereoscopic 3D HD visualization apparatus. These exemplary apparatus can include various optical or electronic magnification systems including stereomicroscopes or can function as open surgery apparatus utilizing overhead cameras with or without magnification.

In conjunction with the multidimensional visualization module, the apparatus includes at least one data processor such as a computer or microprocessor with appropriate software which is configured to produce in real-time, one or more virtual surgical reference indicium including a natural patient vertical in conjunction with the real-time visualization of the target surgical field produced by the exemplary multidimensional visualization module. The data processor is provided with at least one user control input enabling the operating surgeon, or surgical team, to adjust all or at least portions of the pre-operative patient data, including, for example, a still image of the target surgical field, to verify and lock its alignment relative to the multidimensional visualization of the surgical field or to suit the needs or desires of the surgeon or surgical team before or during the surgical procedure involved.

Further, the real-time, virtual surgical reference indicium including natural patient vertical is generated by the at least one data processor utilizing pre-operative patient data. Exemplary pre-operative patient data used to generate the at least one real-time virtual surgical reference indicium and natural patient vertical is generally in the form of a pre-operative still image or, preferably an HD still image, portion of a video clip, or alternatively, an HD photograph, all of which may be stereoscopic 3D images.

Further still, in one embodiment, the HD still image, photo or pre-operative patient data is reviewed or scanned to identify at least one specifically identifiable or distinguishing visual feature such as a scar, vascular pattern, or physical structure found within the target surgical field that is static with respect to the tissues or structures of interest in the surgical procedure. For example, the corneal-scleral junction or "limbus" of the eye is the easily observed boundary or physical junction between the colored tissues of the iris and the surrounding white scleral tissue of the eye and is present in virtually every eye. Similarly, the boundary of the pupil is an easily identifiable physical feature present in all eyes. Such an identifiable visual feature or combination of features is used to align and lock the HD still image or pre-operative patient data in place with the real-time multidimensional visualization of the target surgical field before and during the surgical process to avoid misalignment due to natural structural shifts within the target surgical field.

This initial alignment can be performed by the surgeon, the surgical team, the at least one data processor, or combinations thereof. After the operating surgeon or surgical team verifies the placement of the virtual reference indicium, its position is finalized and locked into place by the operating surgeon prior to initiation of the surgical procedure or during the procedure as appropriate for the indicium involved. Additionally, the operating surgeon or surgical team verifies the placement and alignment of the natural patient vertical, and its position is finalized and locked into place by the operating surgeon prior to initiation of the surgical procedure or during the procedure as appropriate for the indicium involved.

In further accordance with the teachings of the present description, the pre-operative still image now aligned and locked with the real-time multidimensional visualization of the target surgical field is modified to include at least one virtual surgical reference indicium including natural patient vertical which is uniquely suited for the surgical procedure and the specific patient's target anatomy. This modification is accomplished by the data processor or, alternatively, by a second dedicated data processor for generating the surgical reference indicium or multiple reference indicia including natural patient vertical, or by combinations thereof as determined by the surgeon or surgical team. Once incorporated into position, the at least one real-time, virtual surgical reference indicium functions as a reference or guide to assist the surgeon performing the relevant portion of a surgical procedure in spite of the possibility that the target surgical field may have moved or re-oriented relative to other patient physical features or structures after the still image or pre-operative patient data is captured or obtained. Additionally, the included natural patient vertical indicates the true vertical axis of at least a portion of the target surgical structure relative to the target surgical field. The combination of at least one virtual surgical reference indicium with natural patient vertical allows a surgeon to utilize the guidance provided by the virtual surgical reference indicia while being aligned and locked into the true vertical axis of at least a portion of the target surgical structure.

It should be noted that the real-time, virtual surgical reference indicia and natural patient vertical can be presented as two dimensional (2D) or 3D indicia as appropriate or desired. For example, a virtual reference indicium intended to direct a surgical incision of a relative flat tissue can be presented as a 2D line incorporated into the multidimensional or 3D visualization provided by the visualization module. The same hold true for a natural patient vertical. For example, an aligned and locked natural patient vertical can indicate a true vertical axis using a two dimensional line incorporated into the multidimensional or 3D visualization provided by the visualization module. Similarly, surgeons may prefer 3D indicium or natural patient vertical when operating on more complex shapes and surfaces.

Further, the apparatus and methods described herein are ultimately under the control of the operating surgeon and/or surgical team. In some embodiments, the apparatus and associated methods can be fully automated to assist the surgeon or surgical team; however, the ultimate control of the process resides with the operating surgeon and/or surgical team.

Though the methods and apparatus described herein can be applicable to any form of surgery, such as ophthalmologic surgery, corneal transplants, neurosurgery, orthopedic surgery, or car nose and throat surgery, or on any target structure or tissue, the features and advantages are most effectively understood when presented in the non-limiting context of ocular surgery. A particularly illustrative example of the features and benefits is provided by ocular surgical procedures associated with the implantation of an intraocular lens (IOL) into an eye, due to the difficulty in marking the wet curved outer surface of the eye prior to targeting an un-markable internal ocular structure or particular orientation of an eye.

Implantation of an IOL is accomplished utilizing the apparatus and methods described herein by providing the surgeon with at least one real-time multidimensional visualization of at least a portion of an eye including at least a portion of the sclera or white of the eye which includes at least one specific, identifiable visual feature such as a distinct vascular network or pattern of blood vessels observable on the surface of the eye. Then, the pre-operative 3D HD still image is aligned with the at least one specific visual feature in the real-time visualization of the eye during the surgery to maintain the correct orientation of the pre-operative patient data still image with respect to the patient's eye within the 3D HD visualization by matching up the distinctly recognizable pattern or features with their natural counterparts in the real-time visualization. The virtual surgical reference indicium is incorporated into the still image and is correctly aligned with the natural orientation of the target site tissues as a result. The virtual surgical reference indicium includes a natural patient vertical which is aligned and locked to the true measured vertical axis of a patient's eye and thereby assures that a specific ocular surgery is aligned and locked to the patient's natural vertical axis.

Although the virtual surgical reference indicia including natural patient vertical are incorporated into real-time visualization after alignment of the still image in certain exemplary embodiments, in other embodiments, the virtual surgical reference indicia including natural patient vertical are added as early as the capturing of the pre-operative still image. It is within the scope of the present description that the virtual surgical reference indicia including natural patient vertical may be incorporated at any point up until the indicia are needed during a surgical procedure.

The surgeon is then able to utilize the reference indicium including natural patient vertical as a pattern or guide which is aligned and locked into the eye's true vertical axis. In order to make the proper IOL insertion and alignment with the eye's true vertical axis, the indicium including natural patient vertical is accurately dimensioned and aligned with the eye's true vertical axis and visual features of the eye, and incorporated into the 3D HD visualization, rather than being marked directly onto the exterior of the patient's eye as in the prior art where it would at best be an approximation of the dimensions of the underlying structures of interest. Moreover, because the reference indicium including natural patient vertical is virtual, rather than direct, its accuracy, alignment relative to the true vertical axis, position and visibility relative to the IOL being implanted are not affected by the progress of the surgery and remain within the control of the surgeon and or surgical team.

Further advantages and features of the apparatus and methods described herein will be provided to those skilled in the art from a consideration of the following Detailed Description taken in conjunction with the associated Figures, which will first be described briefly.

BRIEF DESCRIPTION OF THE DRAWINGS

FIG. 9A is a front view of a human eye with a chemically dilated pupil illustrating the optical axis of the eye.

FIG. 9 B is a front view of a human eye with a naturally dilated pupil illustrating the line of sight or the visual axis of the eye.

FIG. 9 C is a front view of a human eye illustrating natural cyclorotation.

DETAILED DESCRIPTION

Figure 1:
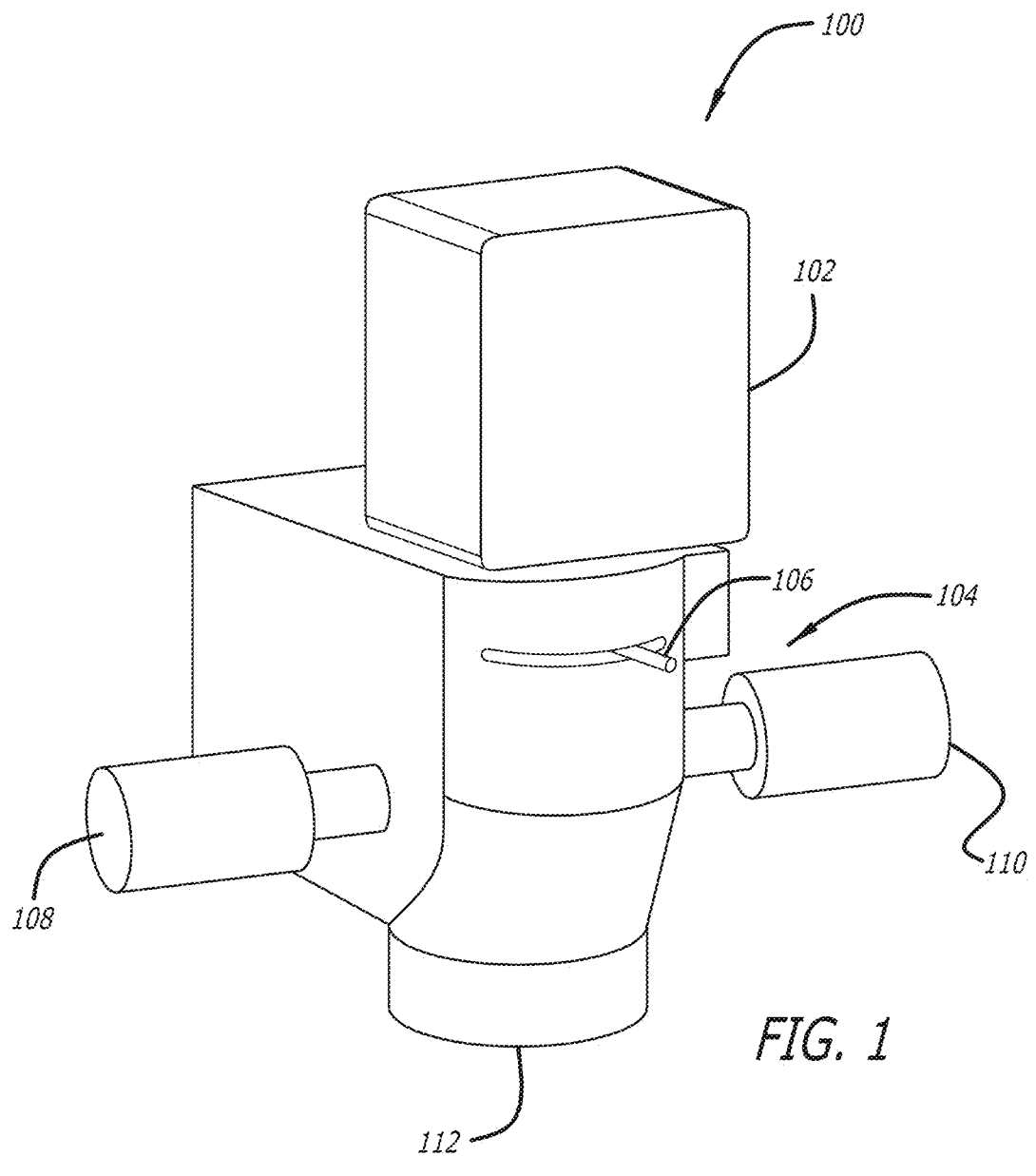
FIG. 1 is an illustration of an apparatus of the present description retrofitted on a surgical microscope.

Described herein are apparatus and methods for the generation of one or more accurate, real-time, virtual surgical reference indicium or multiple virtual surgical reference indicia including at least one natural patient vertical in conjunction with at least one real-time, multidimensional visualization of at least a portion of a target surgical field throughout a surgical procedure or any subpart thereof. In some embodiments, the multidimensional visualization is stereoscopic three-dimensional (3D) video and also may be in high definition (HD). Those skilled in the art will appreciate that a 3D HD real-time visualization will be most effective in enabling a physician to perform a medical or surgical procedure. Moreover, the virtual surgical reference indicia including natural patient vertical can be placed under the direct control and adjustment of the operating surgeon or surgical team, thereby enabling the surgeon to have tight control over the reference indicia and align it to one or more natural patient vertical. Once the surgeon has aligned the virtual surgical reference indicia including natural patient vertical, it can be locked in place and act as an effective guide for the surgeon throughout any or all portions of a surgical procedure at the discretion and control of the surgeon or surgical team.

"Natural patient vertical" as used herein refers to any axis of orientation important to a particular surgical procedure. This axis of orientation can be, for example, a movable tissue's orientation with respect to a particular body part or mark on the body (e.g. a right breast oriented with the left breast to attain symmetry in a breast augmentation procedure), or an orientation of a movable tissue with respect to a particular bone or muscle structure (e.g. an arm oriented with respect to the shoulder blade for reconstructive surgery). In one embodiment according to the present description, natural patient vertical refers to a patient's ocular natural vertical axis, or also referred to as the eye's vertical axis. As used herein, the natural patient vertical, or associated data, is included in the one or more virtual surgical reference indicia described herein. The virtual surgical reference indicia can include information about the natural patient vertical or can be oriented with the natural patient vertical. Virtual surgical reference indicia including natural patient vertical are further described in the embodiments of the present description.

As an added benefit, the real-time virtual surgical reference indicia including natural patient vertical can be positioned accurately at the appropriate depth within the target surgical field to precisely indicate the correct reference indicium size, shape, and position on the tissue or tissues of interest as well as properly align the surgical procedure with the natural patient vertical of the present invention. Further, varying real-time virtual surgical reference indicia including natural patient vertical can be generated within the real-time multidimensional visualization as appropriate during different phases of the surgical procedure where different tissues or structures are subsequently targeted or exposed or to track moving tissues or structures in real-time and to realign the real-time virtual surgical reference indicia as appropriate. Additionally, the color, luminosity, transparency, or other visual characteristics of the virtual reference indicia and natural patient vertical may be altered by a surgeon or the data processor as appropriate to enhance their contrast and visibility relative to the colors and textures of the actual target surgical site to assist the surgeon in performing the surgical procedure.

In a broad aspect, illustrating these beneficial features, an exemplary apparatus incorporates three primary elements: one or more real-time multidimensional visualization modules, one or more data processors, and one or more user control inputs. The three elements can be physically combined into a single device or can be linked as physically separate elements within the scope and teachings of the present invention as required by the specific surgical procedure being practiced.

An exemplary real-time multidimensional visualization module suitable for practicing the present methods incorporates the basic structural components of the Applicant's TrueVision Systems, Inc. real-time 3D HD visualization systems described in the Applicant's co-pending U.S. applications: Ser. No. 11/256,497 entitled "Stereoscopic Image Acquisition Device," filed Oct. 21, 2005; Ser. No. 11/668,400, now U.S. Pat. No. 8,339,447, entitled "Stereoscopic Electronic Microscope Workstation," filed Jan. 29, 2007; Ser. No. 11/668,420, now U.S. Pat. No. 8,358,330, entitled "Stereoscopic Electronic Microscope Workstation," filed Jan. 29, 2007; Ser. No. 11/739,042 entitled "Stereoscopic Display Cart and System," filed Apr. 23, 2007; and Ser. No. 61/042,606, entitled "Apparatus and Methods for Performing Enhanced Visually Directed Procedures Under Low Ambient Light Conditions," filed Apr. 4, 2008, all of which are fully incorporated herein by reference as if part of this specification.

The multidimensional visualization module is used to provide a surgeon with a real-time visualization of at least a portion of a target surgical field, which can be any part of the body of a human or mammalian subject.

"Real-time" as used herein generally refers to the updating of information at essentially the same rate as the data is received. More specifically, "real-time" is intended to mean that the image data is acquired, processed, and transmitted from the photosensor of the visualization module at a high enough data rate and at a low enough time delay that when the data is displayed, objects presented in the visualization move smoothly without user-noticeable judder, latency or lag. Typically, this occurs when new images are acquired, processed, and transmitted at a rate of at least about 30 frames per second (fps) and displayed at a rate of at least about 60 fps and when the combined processing of the video signal has no more than about $\frac{1}{10}^{th}$ second of delay.

It should be appreciated that while it is preferred to utilize a multidimensional visualization module that provides a surgeon with a real-time 3D visualization of at least a portion of the target surgical field, it is contemplated as being within the scope of the present disclosure for the visualization module to provide a real-time visualization that is a real-time 2-dimensional (2D) visualization. However, the use of a 3D visualization is preferred as it provides many benefits to the surgeon including more effective visualization and depth of field. In one embodiment, the visualization of the target surgical field is in high definition (HD).

The term "high definition" or "HD" as used herein can encompass a video signal having a resolution of at least 960 lines by 720 lines and to generally have a higher resolution than a standard definition (SD) video. For purposes of the present invention, this can be accomplished with display resolutions of 1280 lines by 720 lines (720p and 720i) or 1920 lines by 1080 lines (1080p or 1080i). In contrast, standard definition (SD) video typically has a resolution of 640 lines by 480 lines (480i or 480p) or less. It is however, within the scope of the present invention that the multidimensional visualization can be in SD, though HD is preferred.

The apparatuses described herein can be embodied in a single device which can be retrofitted onto existing surgical equipment such as surgical microscopes or open surgery apparatus. This is highly advantageous as the retrofit embodiments can be added to existing systems, allowing expensive equipment to simply be upgraded as opposed to purchasing an entirely new system. The exemplary apparatus can include various optical or electronic magnification systems including stereomicroscopes or can function as open surgery apparatus utilizing cameras and overhead visualizations with or without magnification.

FIG. 1 illustrates retrofitted surgical microscope 100 incorporating image capture module 102 which includes a multidimensional visualization module and an image processing unit, both housed within image capture module 102, and therefore, not depicted. The exemplary image capture module comprises at least one photosensor to capture still images, photographs or videos. As those skilled in the art will appreciate, a photosensor is an electromagnetic device that responds to light and produces or converts light energy into an electrical signal which can be transmitted to a receiver for signal processing or other operations and ultimately read by an instrument or an observer. Image capture module 102 is secured to surgical microscope 104 in place of the microscope's binocular eyepiece. Although surgical microscope 104 has been retrofitted with image capture module 102, it still retains the use of conventional controls and features such as, but not limited to, iris adjustment knob 106, first adjustment knob 108, second adjustment knob 110 and objective lens 112.

Figure 2:
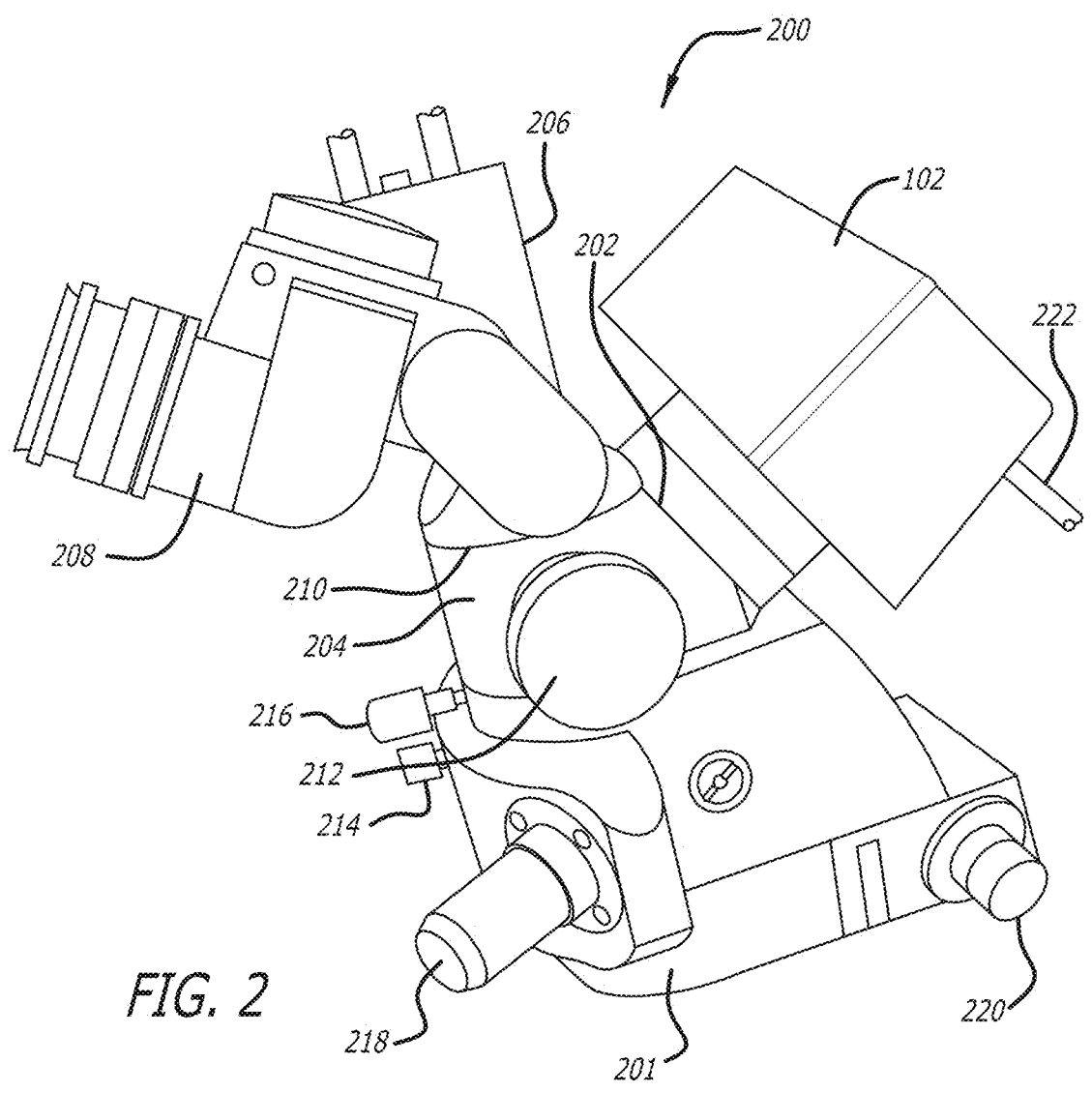
FIG. 2 is another illustration of an apparatus of the present description retrofitted on a different surgical microscope.

In another embodiment, FIG. 2 illustrates second retrofitted surgical microscope 200 incorporating image capture module 102 retrofitted onto second surgical microscope 201. Surgical microscope 201 is retrofitted with image capture module 102 coupled to first ocular port 202 on ocular bridge 204. Further, ocular bridge 204 couples video camera 206 to a second ocular port (not shown) and binocular eyepiece 208 to third ocular port 210. Optional forth ocular port 212 is available for further retrofits to surgical microscope 201. Although surgical microscope 201 has been retrofitted with image capture module 102, it still retains the use of conventional controls and features such as, but not limited to, iris adjustment knob 214, first adjustment knob 216, second adjustment knob 218, illumination control knob 220, and an objective lens (not shown). Further still, image capture module 102 can send a receive information through signal cable 222.

Figure 3:
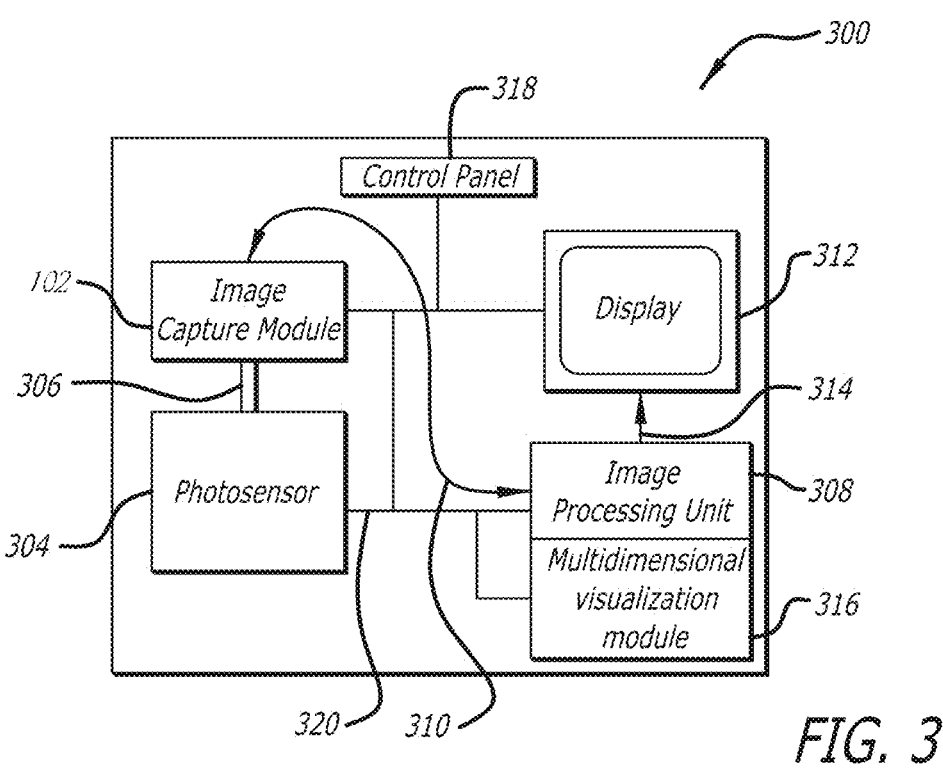
FIG. 3 is a schematic overview of an exemplary embodiment of an apparatus of the present description illustrating features thereof.

An exemplary, non-limiting configuration of components is illustrated in FIG. 3. Apparatus setup 300 includes image capture module 102, coupled to photosensor 304 by bi-directional link 306. Those skilled in the art will appreciate that bi-directional link 306 can be eliminated where image capture module 102 and photosensor 304 are physically the same device. Image capture module 102 is in direct communication with image processing unit 308 by first cable 310. First cable 310 can be a cable connecting to physically different devices, can be a cable connecting two physically different components within the same device, or can be eliminated if image capture module 102 and image processing unit 308 are physically the same device. First cable 310 allows, in certain embodiments, bi-directional communication between image capture module 102 and image processing unit 308. Image processing unit 308 generates images and videos that are displayable on display 312. It is within the scope of the present description that display 312 include multiple displays or display systems (e.g. projection displays). An electrical signal (e.g. video signal) is transmitted from image processing unit 308 to display 312 by a second cable 314, which is any kind of electrical signal cable commonly known in the art. Image processing unit 308 can be in direct communication with multidimensional visualization module 316, which can also send electrical signals to display 312 via second cable 314. In one embodiment, image capture module 102, image processing unit 308, and multidimensional visualization module 316 are all housed in a single device or are physically one single device. Further, one or all of the components of the present invention can be manipulated by control panel 318 via cable network 320. In one embodiment, control panel 318 is wireless.

"Display," as used herein, can refer to any device capable of displaying a still or video image. Preferably, the displays of the present disclosure display HD still images and video images or videos which provide a surgeon with a greater level of detail than a SD signal. More preferably, the displays display such HD stills and images in 3D. Exemplary displays include HD monitors, cathode ray tubes, projection screens, liquid crystal displays, organic light emitting diode displays, plasma display panels, light emitting diodes, 3D equivalents thereof and the like. In some embodiments, 3D HD holographic display systems are considered to be within the scope of the present disclosure. In one embodiment, display 312 is a projection cart display system and incorporates the basic structural components of the Applicant's True Vision Systems, Inc. stereoscopic image display cart described in the Applicant's co-pending U.S. application: Ser. No. 11/739,042, entitled "Stereoscopic Display Cart and System" filed Apr. 23, 2007, which is fully incorporated herein by reference as if part of this specification.

The exemplary image processing units as illustrated in FIGS. 1, 2 and 3 include a microprocessor or computer configured to process data sent as electrical signals from image capture module 102 and to send the resulting processed information to display 312, which can include one or more visual displays for observation by a physician, surgeon or a surgical team. Image processing unit 308 may include control panel 318 having user operated controls that allow a surgeon to adjust the characteristics of the data from image capture module 102 such as the color, luminosity, contrast, brightness, or the like sent to the display.

In one embodiment, image capture module 102 includes a photosensor, such as a camera, capable of capturing a still image or video images, preferably in 3D and HD. It is within the teachings herein that the photosensor is capable of responding to any or all of the wavelengths of light that form the electromagnetic spectrum. Alternatively, the photosensor may be sensitive to a more restricted range of wavelengths including at least one wavelength of light outside of the wavelengths of visible light. "Visible light," as used herein, refers to light having wavelengths corresponding to the visible spectrum, which is that portion of the electromagnetic spectrum where the light has a wavelength ranging from about 380 nanometers (nm) to about 750 nm.

More specifically, the one or more data processors are also in direct communication with multidimensional visualization module 316 and/or image capture module 102. The data processors, in their basic form, are configured to produce one or more real-time virtual surgical reference indicium including at least one natural patient vertical in conjunction with the real-time visualization of at least a portion of the target surgical field produced by multidimensional visualization module 316. In one embodiment, the data processor or processors are incorporated into multidimensional visualization module 316. In another embodiment, at least one data processor is a stand alone processor such as a workstation, personal data assistant or the like.

The one or more data processors are controlled by built-in firmware upgradeable software and at least one user control input, which is in direct communication with the data processors. The at least one user control input can be in the form of a keyboard, mouse, joystick, touch screen device, remote control, voice activated device, voice command device, or the like and allows the surgeon to have direct control over the one or more virtual surgical reference indicium including natural patient vertical.

Figure 4:
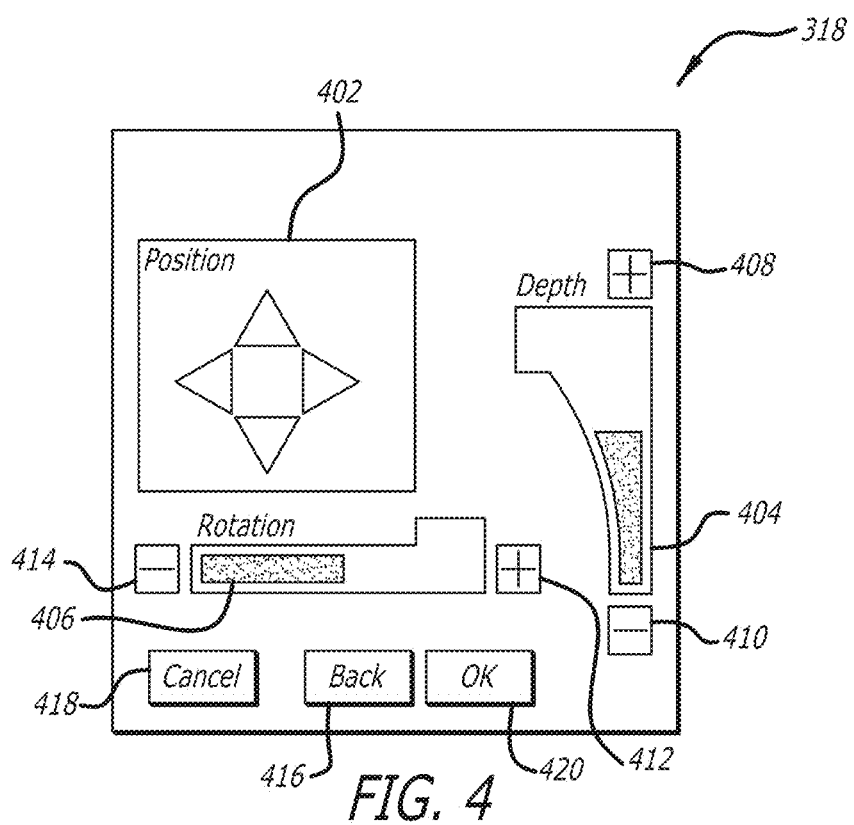
FIG. 4 is a plan view of an exemplary alignment control panel of the present description illustrating an exemplary embodiment of user input control thereof.

FIG. 4 illustrates an exemplary user control input, in the form of control panel 318. Control panel 318 includes multidirectional navigation pad 402 with user inputs allowing a controlling surgeon or operator to move data vertically, horizontally or any combination of the two. Additionally, the depth of the data can be adjusted using depth rocker 404 of control panel 318 and the rotation can be adjusted using rotation rocker 406 of control panel 318. Depth can be adjusted using both increase depth position 408 and decrease depth position 410 of depth rocker 404. Additionally, rotation can be adjusted using both increase rotation position 412 and decrease rotation position 414 of rotation rocker 406. Other non-limiting adjustments that can be made to the pre-operative image or to the real-time visualization include changes in diameter, opacity, color, horizontal and vertical size, and the like, as known in the art. It should be noted that in exemplary control panel 318 an adjustment can be undone by the surgeon utilizing "back" button 416. Further, the entire process can be ended by the surgeon by engaging "cancel" button 418. Further, once the surgeon is satisfied with the alignment of the data, the alignment is locked into place by engaging "ok" button 420.

Alternative control panel embodiments for the manipulation and alignment of the pre-operative still image are contemplated as being within the scope and teachings of the present description. For example, a hand-held device such as a 3D mouse can be used as known in the art to directly position templates, images, and references within the real-time multidimensional visualization. Such devices can be placed on a tabletop or held in mid-air while operating. In another embodiment, foot switches or levers are used for these and similar purposes. Such alternative control devices allow a surgeon to manipulate the pre-operative still image without taking his or her eyes off of the visualization of a surgical procedure, enhancing performance and safety.

In yet another alternative embodiment, a voice activated control system is used in place of, or in conjunction with, control panel 318. Voice activation allows a surgeon to control the modification and alignment of the pre-operative still image and its associated indicia as if he was talking to an assistant or a member of the surgical team. As those skilled in the art will appreciate, voice activated controls typically require a microphone and, optionally, a second data processor or software to interpret the oral voice commands. In yet a further alternative embodiment, a system is envisioned wherein the apparatus utilizes gesture commands to control pre-operative image adjustments. Typically, as known in the art, the use of gesture commands involves an apparatus (not shown) having a camera to monitor and track the gestures of the controlling physician and, optionally, a second data processor or software to interpret the commands.

In one embodiment, apparatus setup 300 can be used in many medical settings. For example, apparatus setup 300 can be used in an examination room. Therein, image capture module 102 utilizes photosensor 304 to capture pre-operative patient data such as still images, preferably in HD, and information relating to natural patient vertical. Photosensor 304 can be coupled to any piece of medical equipment that is used in an examination room setting wherein pre-operative data can be captured. Image capture module 102 directs this data to image processing unit 308. Image processing unit 308 processes the data received from image capture module 102 and presents it on display 312.

In another embodiment, apparatus setup 300 can be used in an operating room. Therein, image capture module 102 utilizes photosensor 304 to capture a real-time visualization of at least a portion of the target surgical field, preferably in HD, more preferably in 3D. Image capture module 102 directs this data to image processing unit 308 including multidimensional visualization module 316. Image processing unit 308 including multidimensional visualization module 316 processes the data received from image capture module 102 and presents it on display 312 in real-time.

In one exemplary embodiment, apparatus setup 300 is used in an operating room and photosensor 304 is a surgical microscope. Therein, image capture module 102 is retrofitted on the surgical microscope. The use of a surgical microscope in combination with apparatus setup 300 allows a surgeon to comfortably visualize a surgical procedure on one or more displays instead of staring for, in some cases, several hours though the eyepiece of a surgical microscope.

Apparatus setup 300 used in an examination room can be in direct communication with apparatus setup 300 used in the operating room. The two apparatus setups can be directly connected by cable, or indirectly connected through an intermediary device such as a computer server. In some embodiments, the two sections can be separate systems, even in different physical locations. Data can be transferred between the two systems by any means known to those skilled in the art such as an optical disc, a flash memory device, a solid state disk drive, a wired network connection, a wireless network connection or the like.

A further understanding of the present disclosure will be provided to those skilled in the art from an analysis of exemplary steps utilizing the apparatus described above to practice the associated methods disclosed herein.

Though the apparatus and associated methods are applicable to any type of surgery on any target structure or tissue, the exemplary features and advantages will be disclosed in the illustrative, but non-limiting context of ocular surgery particularly phakic and aphakic intraocular lens (IOL) implantation. This type of surgical procedure is quite common. For example, there are over three million IOL implantation procedures done per year in the United States.

The apparatus and methods described herein are specifically adaptable for use in performing IOL implantation without modification. As first steps in an aphakic IOL implantation procedure, both a capsulorrhexis and phacoemulsification or equivalent procedures are performed. In a phakic IOL implantation, only a corneal incision is performed because the natural crystalline lens remains intact.

Figure 5:
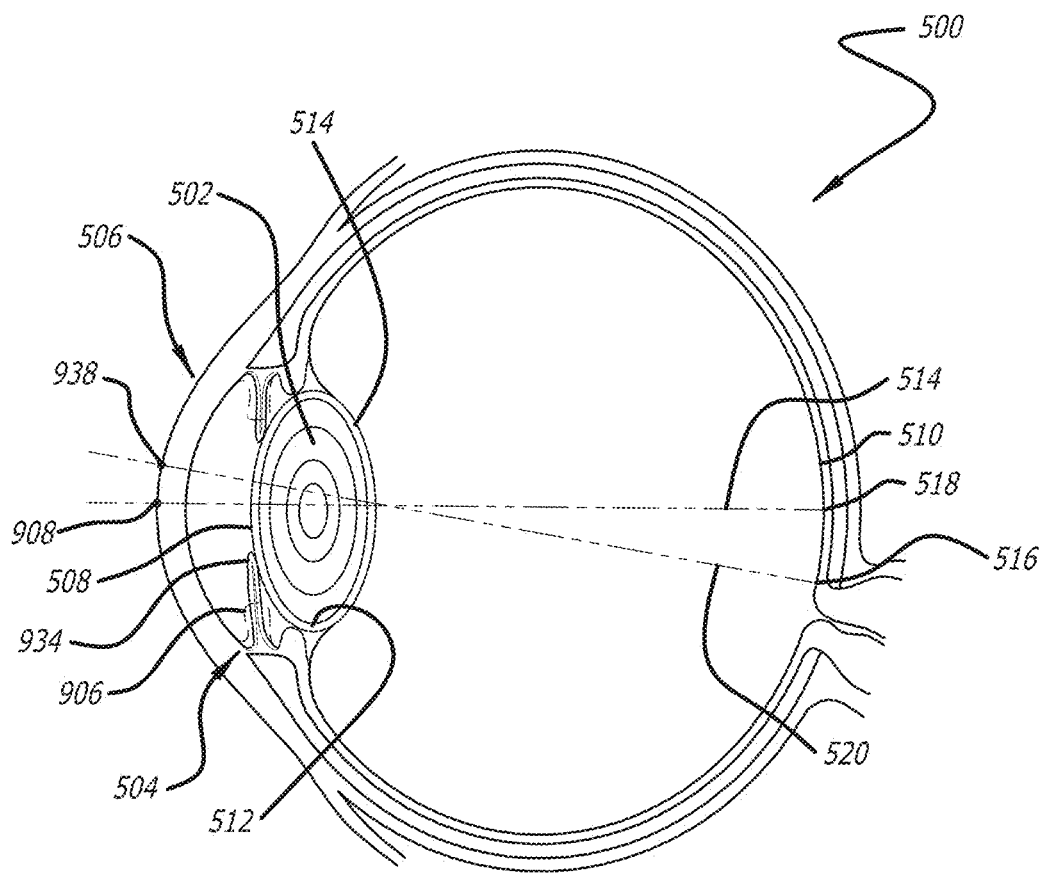
FIG. 5 is a cross-section of a human eye illustrating its structural elements and features including the optical axis and the line of sight.

Referring to FIG. 5, a cross-sectional view of a general structure of eye 500 is provided. Should eye 500 stop functioning due to problems with natural crystalline lens 502, such as the development of a cataract, it may become necessary for an ocular surgeon to remove natural crystalline lens 502 by performing a capsulorrhexis and subsequent phacoemulsification. In such procedures, to remove a damaged or opaque natural crystalline lens 502 from eye 500, an ocular surgeon first makes at least one small incision at the limbus or corneal-sclera junction 504 at the border or edge of cornea 506. This incision is made with a tool known as a microtome or with a diamond scalpel in order to gain access to natural crystalline lens 502. Through this incision the surgeon can access the front of natural crystalline lens 502 with another surgical tool such as capsulorrhexis forceps that grasp or engage anterior capsule 508. Anterior capsule 508 is a thin transparent membrane covering the front of natural crystalline lens 502 much like the peel of a grape. In a capsulorrhexis procedure at least a portion of anterior capsule 508 is grasped and torn away to expose underlying natural crystalline lens 502 for subsequent removal via phacoemulsification.

In the early days of capsulorrhexis procedures, anterior capsule 508 was simply torn away and removed as part of natural crystalline lens 502 removal process in order to eventually allow light to once again pass through to retina 510 to restore sight in the patient's eye. In those early days, there was no need to be particularly concerned with the details taken in removing anterior capsule 508 as long as the capsulorrhexis provided the surgeon with sufficient access to remove natural crystalline lens 502. In the early days of cataract surgery, after natural crystalline lens 502 was completely removed, the patient was required to wear heavy "cataract glasses" or contact lenses for subsequent vision correction in the now lens-less or "aphakic" eye.

In the 1970s there was an explosion of development directed toward replacement of natural crystalline lens 502 with pseudophakic or synthetic lenses that were implanted in place of the removed natural crystalline lens. These pseudophakic or artificial lenses came to be known as intraocular lenses or "IOLs".

Later, development of an IOL that rested atop natural crystalline lens 502 was developed to correct vision problems without the need for contact lenses or heavy prescription glasses. Such IOLs are termed phakic IOLs, implantable contact lenses, or "ICLs" because natural crystalline lens 502 is not removed, but rather the implanted lens supplements natural crystalline lens 502.

Figure 6:
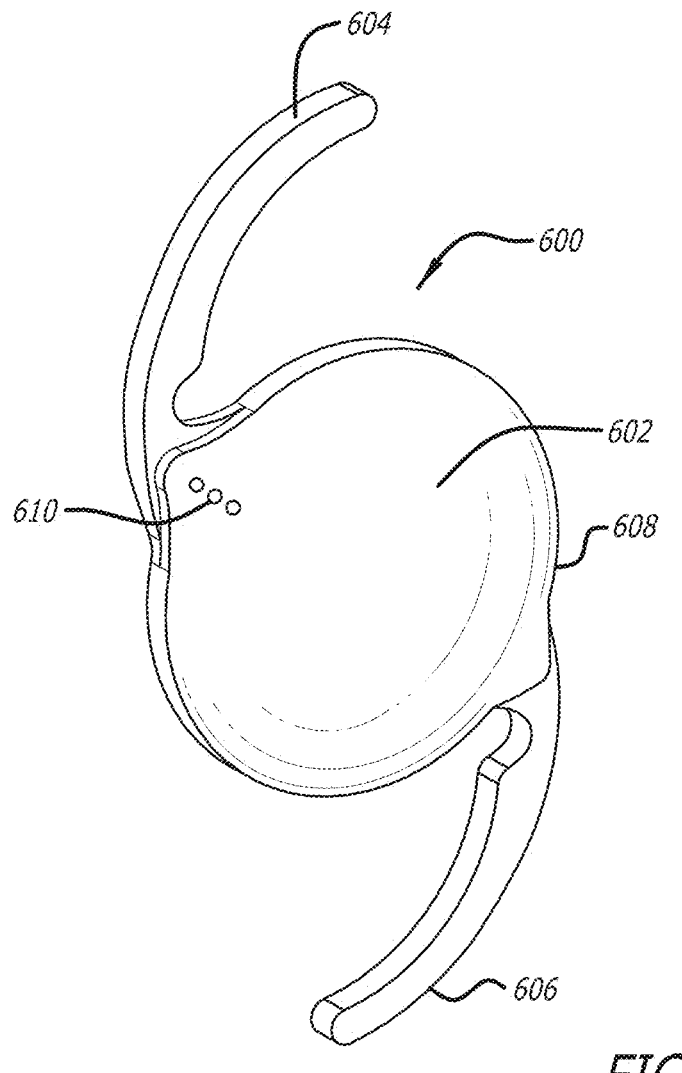
FIG. 6 is an illustration of an intraocular lens (IOL).

The majority of IOLs in use are "aphakic" IOLs. An aphakic IOL is generally an implanted lens that rests in the position previously occupied by natural crystalline lens 502, after natural crystalline lens 502 is surgically removed as a result of a cataract or injury. FIG. 6 depicts a general structure of IOL 600. IOL 600, includes optic portion 602 wherein light is passed through, and, depending on the focal length of the lens needed to focus the light onto retina 510, (FIG. 5) optical portion 602 is curved accordingly. First haptic 604 and second haptic 606 are connected to circumferential edge 608 of optic portion 602. First haptic 604 and second haptic 606 are used to position, orient and anchor IOL 600 within capsular bag 512. There are several IOL designs with different numbers of haptics and orientations of optic portion 602 relative to circumferential edge 608 known in the art. IOL 600 may also include one or more orientation markings 610 which is useful by a surgeon in properly aligning IOL 600 once implanted within capsular bag 512 (FIG. 5).

Generally, first haptic 604 and second haptic 606 are positioned within the annular recesses of capsular bag 512 formed by anterior capsule 508 and posterior capsule 514 originally surrounding natural crystalline lens 502 (FIG. 5). Because of this, it became important to leave a rim of tissue formed by an annular portion of the anterior membrane in place in order to maintain the placement of first haptic 604 and second haptic 606 to secure the positioning of IOL 600. Without a rim of anterior capsular tissue, IOL 600 could not be anchored in place and could possibly end up floating around the anterior portion of the eye with no benefit, or even deleterious effects, to the patient.

Figure 7:
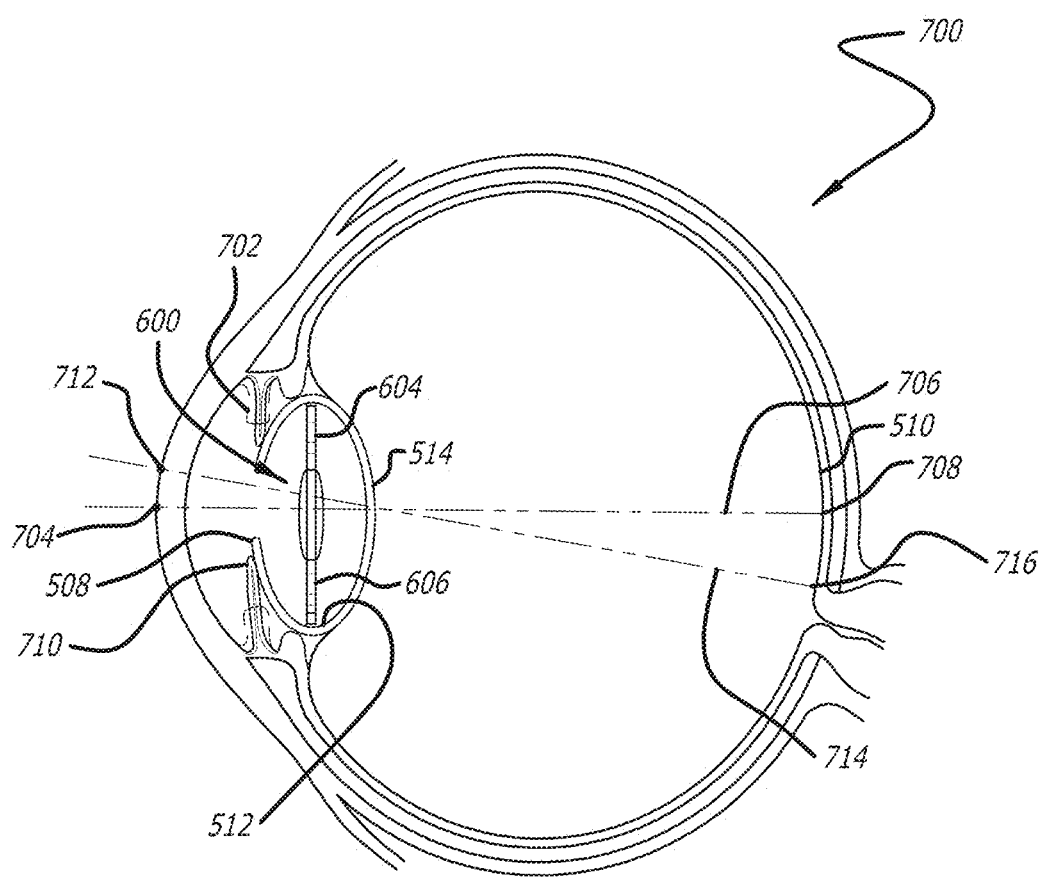
FIG. 7 is a cross-section of a human eye illustrating an implanted IOL.

A typical IOL, such as, for example, IOL 600, in dilated eye 700 of FIG. 7 has first haptic 604 and second haptic 606 positioned properly in the annular recesses of capsular bag 512 formed by anterior capsule 508 and posterior capsule 514. Commonly in current IOL implantation outcomes, under chemical dilation, symmetrically dilated pupil 702 allows light to pass through substantially the center of IOL 600 via optical axis center point 704. As light enters symmetrically dilated pupil 702, it passes through optical axis center point 704, travels along optical axis 706 and hits retina 510 at retinal center point 708. In contrast, under normal conditions without chemical dilation, asymmetrically dilated pupil 710 allows light to pass through IOL 600 via natural line of site center point 712. Therefore, light traveling through asymmetrically dilated pupil 710 along visual axis 714, will not pass through the center of IOL 600. Rather, it will pass through the edge of IOL 600 and focus on focal point 716 potentially causing visual acuity problems and complications for the patient.

However, as IOL designs improve and become more complex, capsulorrhexis placement, shape, and size become more important as does the orientation of the implanted IOL. Modern IOLs can be multi-focal designs with areas having different optical properties much like bifocal glasses with different corrective factors on the top and bottom of their optic portion 602. With IOLs, however, the outer peripheral portion of the generally circular lenses have one focal correction factor while the centers have another, different focal factor providing bi-focal tri-focal vision, or even more levels of focal distance often without glasses. As such, it becomes increasingly more important to line an IOL up with a patient natural vertical.

Figure 8:
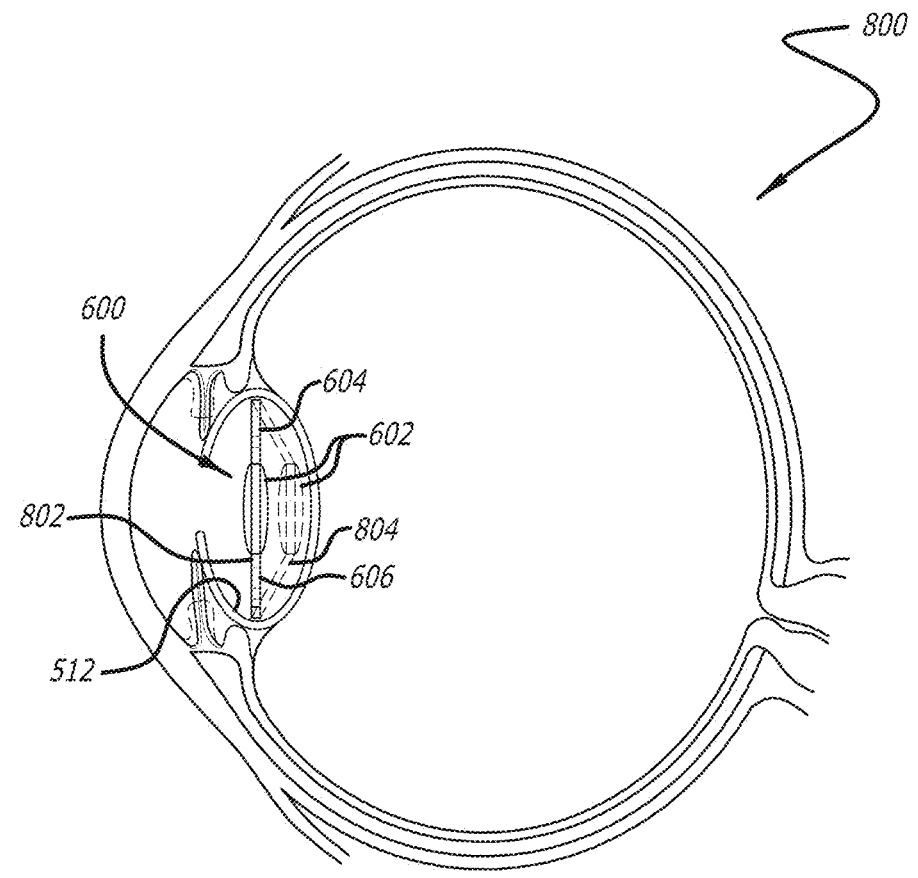
FIG. 8 is a cross-section of a human eye illustrating an implanted vaulting IOL.

The most current IOL designs are known as accommodating lenses in that first haptic 604 and second haptic 606 can flex in response to normal muscular contractions within the structures of the eye surrounding IOL 600 causing optic portion 602 to move forward and back within the eye, a process known as "vaulting." FIG. 8 illustrates implanted eye 800, wherein IOL 600 vaults from natural position 802 to second position 804. As IOL 600 vaults, first haptic 604 and second haptic 606 need to flex accordingly yet still remain anchored within capsular bag 512. As such, the placement, size, and shape of the capsulorrhexis tear is important as well as the orientation of the lens within capsular bag 512. Thus, such lenses function much like the natural crystalline lens by effectively changing focal length to accommodate near and far vision. Accurate placement and retention of such modern accommodating IOL designs is important to their function, to the patient's subsequent visual acuity, and ultimately to the patient's satisfaction with the IOL implantation surgery.

With this understanding of the contemporary need for accurately and precisely placed, and accurately oriented and aligned IOLs, the following non-limiting, exemplary embodiments illustrate the previously unobtainable features and advantages of the apparatus and methods with relation to providing at least one accurate, real-time virtual surgical reference indicium including one or more natural patient vertical that can guide a surgeon in performing a properly and accurately aligned IOL implantation.

As a first step in an IOL implantation according to the present description, a pre-operative data set is captured or obtained. The pre-operative data set can include any portion of data about a patient including, for example, the patient's weight, age, hair color, bodily features, medical history, and at least one image of at least a portion of the patient's target surgical anatomy, specifically the eye, information about axes of the eye of the patient, and the like. According to one embodiment, the pre-operative data set includes at least one natural patient vertical of the patient's eye. Natural patient vertical as used herein is a measurement based at least partially on natural line of sight incorporating the patient's natural visual axis relative to changes in orientation of the target surgical field or the visual axis itself, thereby tracking the true vertical axis of the eye regardless of where it shifts. A natural patient vertical is indicated in chemically dilated eye 900 of FIG. 9A by vertical axis identifier 902.

In an exemplary embodiment, the pre-operative dataset, or pre-operative patient data includes a still image of at least a portion of the eye of the patient undergoing a optical procedure along with a measurement of the natural patient vertical. In some embodiments, the pre-operative still image is in HD. A pre-operative data set can also include a mark-up of the patients target surgical site for analysis, measurement, or alignment as well as topographical data or measurements.

In most known ocular procedures, a significant preliminary pre-operative step is to conduct a pre-operative examination of the patient's eye to identify, among other things, natural patient vertical. It will be appreciated by those skilled in the art that natural patient vertical, which incorporates the optical axis, and the visual axis of an eye are not necessarily synonymous or identical. In fact they vary depending upon ambient light conditions and may diverge from one another depending on the nature of pupil dilation.

"Dilation" of an eye is a retraction of the iris, opening the pupil of the eye and allowing more light to reach the retina. In most surgery conducted under bright ambient lighting; pupil dilation is commonly accomplished using chemical dilating agents to relax the iris sphincter muscle thereby increasing the circumference of the iris to a maximal extent. In this manner the surgeon is provided with a clear view and subsequent access to internal structures of the eye.

However, chemically induced pupil dilation produces a markedly different shaped pupil and pupillary boundary as well as a different pupillary center point location from that produced by natural dilation. For example, as illustrated in FIG. 9A (reference is also made to FIG. 7), chemically dilated eye 900 has dilated iris 904 that produces a large, generally symmetrical pupil 906 concentric with the observed optical axis center point 908. This corneal center reference point is very close to that defined by the geometric center of the circle formed by the intersection of the patient's "limbus", the junction of the cornea and the sclera or "white" of the patient's eye. As depicted in FIG. 5, optical axis 514 is defined by a line connecting the anterior pole, or optical axis center point 908, and the posterior poles, or retinal center point 518, of the eye. Further, natural patient vertical is generally in an upright configuration as indicated by vertical axis identifier 902. As will be discussed, this vertical axis can shift, or reorient, depending on the patient's orientation.

In contrast to symmetrical chemical dilation, naturally dilated eye 930, as shown in FIG. 9B, generally presents itself in low ambient light or no light conditions where natural dilated iris 932 naturally retracts to a lesser extent than under chemical dilation. More importantly, naturally dilated eye 930 is not symmetrical and produces asymmetrical pupil 934 that is generally biased nasally (towards the nose) and superiorly (up from center) as indicated by arrow 936 relative to symmetrical pupil 906 shown in FIG. 9A and is generally unique for each patient. As a result of this asymmetrical dilation, the patient's natural line of sight center point 938 as defined in the patient's cornea by the center of asymmetrical pupil 934 is also biased away from observed optical axis center point 908 observed under chemical dilation in FIG. 9A. Therefore, under non-chemical dilation conditions, a patient's optical and visual axis corneal center points may not, and typically do not, line up.

This difference between an observed optical axis center point 908 and natural line of sight center point 938 is further illustrated by the cross-sectional view of eye 500 illustrated in FIG. 5. There, the chemically-induced observed optical axis center point 908 is illustrated as being generally centrally disposed at the center of cornea 506 as defined by the chemically induced symmetrical pupil 906. In contrast, natural line of sight center points 938 is shown at a position that is generally nasally and superiorly biased away from observed optical axis center point 908 near the center of cornea 506 as defined by natural asymmetrical pupil 934. The resulting visual axis 520 passes through natural line of sight center point 938 and terminates at focal point 516 of eye 500. As those skilled in the art will appreciate, surgical procedures designed to improve or restore a patient's vision will be more effective if the procedures are based upon the patient's true or natural line of sight center point 938 as opposed to chemically induced observed optical axis center point 908 that has a lesser relation to how the patient's eye naturally focuses light to the high resolution focal point of the patient's retina at fovea, or focal point 516. As will be discussed, the vertical axis identifier 902 can shift depending on the patient's orientation.

Further, complicating matters and contributing to the possibility of less than optimal patient outcomes and post-surgical visual acuity is another natural phenomenon of the human eye known as cyclorotation or cyclotorsion. Cyclorotation refers to the condition where, when a patient lays down from a generally vertical orientation into a supine or generally horizontal position, the patient's eyes will rotate away from the measured vertical axis by a variable amount which ranges from about −12 to +12 degrees.

FIG. 9C illustrates this phenomenon of cyclorotation as eye 960 rotates away from the normal or originally measured vertical axis 968 by variable angle 962 when a patient assumes a prone or supine position. This rotation is further illustrated by the shifting of observable or visual scleral features 964 and 966 which also have rotated by variable angle 962. Thus, originally measured vertical axis 968 of the patient's eye, generally taken with the patient sitting in a vertical orientation, and any associated physical or structural aberrations and the resultant spherical distortions or astigmatism measured relative thereto, can differ from those of observed vertical axis 970, of the eye when the patient lays down into a supine or generally horizontal position, where most ocular surgeries take place, and the target eye cyclorotates into this displaced orientation. The present apparatus and methods make it possible for the surgeon to maintain the proper orientation, or natural patient vertical, of corrective procedures relative to the patient's originally measured vertical axis 968 by providing appropriately aligned reference indicia including natural patient vertical which is aligned to observed vertical axis 970.

Prior to the present description, it was the individual and variable skill of the surgeon at compensating for these natural physical differences between measured optical and vertical axis during the surgical procedure that determined the degree of post-operative success of the procedures involved in the ocular surgery and the resultant degree of patient satisfaction with the procedure. Natural patient vertical was rarely, if ever, taken into account during a surgical procedure.

In rare cases, in an attempt to overcome this shifting of natural patient vertical in the past, a marker or pen was used to draw on the sclera (the white or opaque part of the eye) to indicate the seated visual axis of the eye. The hope was that upon assuming a supine position for surgery the marked indication of visual axis would shift and the surgeon could compensate accordingly based upon his experience. However, the abundance of natural tears and surgical fluids such as saline solution often caused the marking to run or dissolve, making such prior art techniques inaccurate and variable at best.

The present description specifically overcomes these problems by providing a surgeon with the ability to create and use one or more user adjustable, accurate, real-time, virtual surgical reference indicium including natural patient vertical which clearly and accurately take into account the true vertical axis of the patient despite any shifting due to cyclorotation or asymmetrical dilation resulting from changes in the patient's physical positioning between pre-operative examination and surgery.

In one embodiment, wherein a pre-operative data set is collected, in order to properly measure natural patient vertical and other pre-operative data, a slit lamp microscope is used to collect the data. A "slit lamp" is an instrument commonly consisting of a high intensity light source that can be adapted to focus and shine the light as a slit. A slit lamp allows an optometrist or ocular surgeon to view parts of the eye in greater detail than can be attained by the naked eye. Thus, a slit lamp can be used to view the cornea, retina, iris and sclera of a patient's eye or to measure natural patient vertical and the optical or visual axis of a patient. A conventional slit lamp can be retro-fitted with an image capture module as described herein, preferably with at least one photosensor. This allows a surgeon or optometrist to comfortably collect accurate and reliable pre-operative patient data including at least one still image of the patient's eye and natural patient vertical, preferably under natural dilation and most preferably in HD.

This is best accomplished under natural dilation or with an un-dilated iris to clearly view and examine the patient's eye in low ambient light because the exemplary visualization modules described herein are able to produce an accurate 3D HD image in at least one wavelength outside of the wavelengths of visible light. As an added benefit, collecting the pre-operative patient data under low ambient light conditions accurately identifies the patient's natural patient vertical for subsequent tracking and reference without sacrificing visual acuity for the physician.

In a second step, the pre-operative data set still image, or just still image, captured in the first step is matched to a real-time multidimensional visualization of at least a portion of the target surgical field. Matching the still image to the multidimensional visualization is important because the target surgical field may have changed since the pre-operative image still was captured such as by tissue shifting and rotating when the patient changes position. As a result, the measurements obtained during the pre-operative examination may no longer be accurate or easily aligned in light of such changes in the patient's physical alignment and position. Additionally, any surgical markings that may have been applied to the patient's tissues during the pre-operative examination may have shifted, been wiped away, or blurred.

At this point, the pre-operative still image of the patient's eye is analyzed by a surgeon, a surgical team or the at least one data processor of the apparatus to identify at least one distinct visible feature that is static and recognizable relative to and within the target surgical field. Utilizing the teachings described herein, this at least one distinct visible feature is used to align the image with the real-time multidimensional visualization of the target surgical field during the actual surgery. Preferably, this real-time visualization is a 3D HD visualization of the target surgical field.

For example, referring to FIG. 9A, one or more exemplary distinct visible features that can be identified are illustrated in sclera 910 (the white region of the eye) of eye 900. However, recognizable visible features can also be identified within the iris, on the cornea, or on the retina of the eye. Exemplary distinct visible features include, without limitation, surface vasculature 912, visible vascular networks 914 and vascular branching patterns 916, iris patterns 918, scratches on the cornea, dimples on the cornea, retinal features 920, deformities, voids, blotches, sequestered pigment cells, scars, darker regions, and combinations thereof. Additionally, corneal-scleral junction 922, or boundary known as the limbus, and pupillary boundary 924 are additional distinct visible features that can be utilized in accordance with the teachings of the present invention to align and track the image in conjunction with the real-time visualization of the target surgical field.

In one embodiment, once at least one distinct visible feature has been identified in the pre-operative patient data still image, the still image and the associated visible feature or features are stored for later processing and use in the operating room. It should be noted that the pre-operative patient data need not be taken in a separate operation or at a separate location from the operating room or theater. For example, during surgery to repair a traumatic injury, the entire process can be performed in the operating room to save time.

A third step involves the surgeon, the surgical team, the at least one data processor, or a combination thereof aligning the pre-operative still image of the target surgical field with the real-time multidimensional visualization of the target surgical field. Generally speaking, this alignment is accomplished utilizing specific static visual features identified within the pre-operative still image of the target surgical site to align the still image with the real-time multidimensional visualization of the target surgical field. This allows the pre-operative image to be aligned accurately with the tissues of the target surgical field regardless of whether the target surgical field has shifted, rotated or reoriented relative to other patient tissues or structures following collection of the pre-operative data. Whatever method is used to align the pre-operative image with the real-time visualization, the ultimate authority to modify the image and to lock the alignment in place rests in the hands of the surgeon in control of the procedure.

Figure 10:
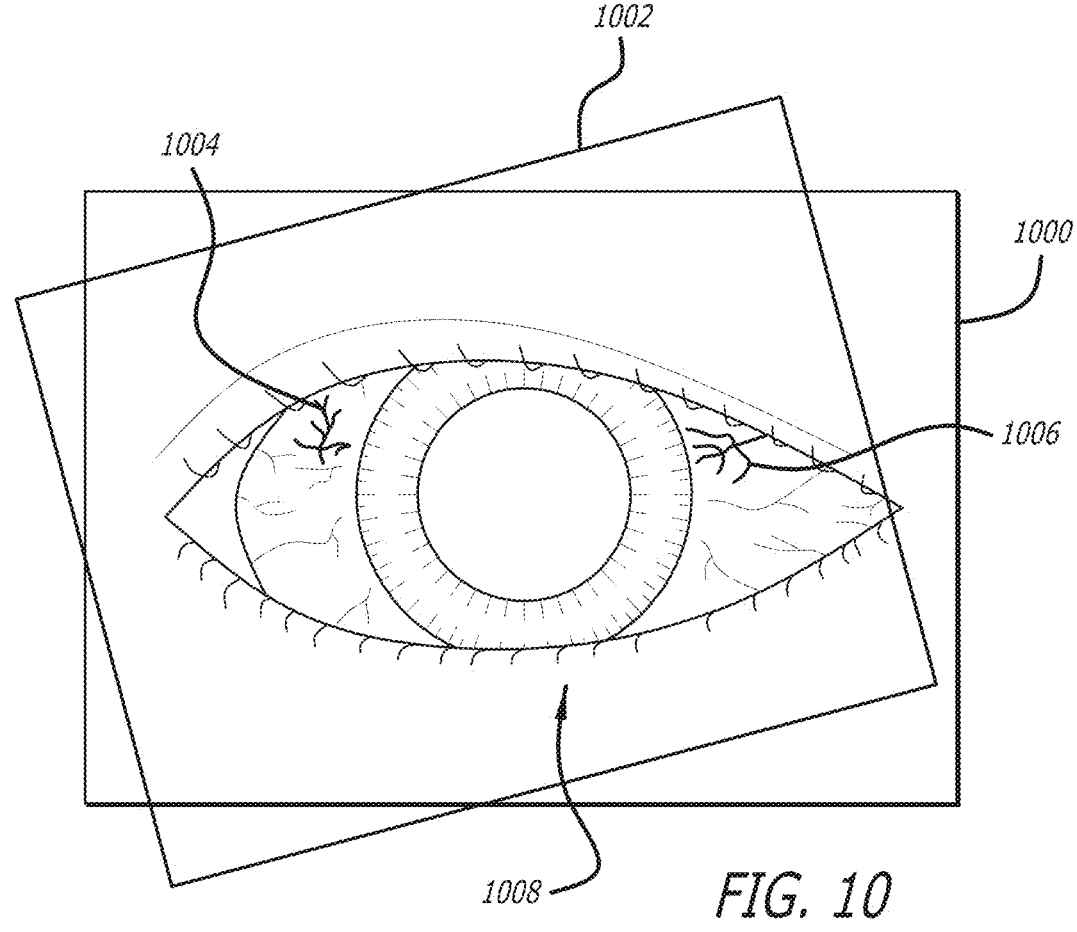
FIG. 10 is a front view of a human eye of a patient illustrating an exemplary embodiment of a real-time 3D HD visualization overlaid with an aligned HD pre-operative patient data still image of the patient eye.

The pre-operative still image of the patient's eye is overlaid on one or more real-time 3D HD visualizations of at least a portion of the patient's target surgical field for at least a portion of the surgical procedure. Referring to FIG. 10, exemplary real-time 3D HD visualization 1000 of a patient's eye is overlaid with pre-operative patient data still image 1002 of the same eye. Previously identified and recognizable distinct vascular networks in the sclera of the patient's eye, identified on the left as reference numeral 1004 and on the right as reference numeral 1006 of eye 1008 are used to align pre-operative patient data still image 1002 with real-time 3D HD visualization 1000.

It should be noted that pre-operative patient data still image 1002 is shown as being rotated relative to real-time 3D HD visualization 1000, for example by a surgeon, to account for the naturally occurring cyclorotation of the patient's target eye as a result of the patient lying down for surgery. The previously identified distinct visual features 1004 and 1006 are used to rotate and align patient data still image 1002 with the corresponding static visible structures of the patient's eye to maintain close alignment of the target site with the measured optical and visual axes and the associated structural and physical features of the patient's eye. Once the still image has been properly aligned either by a surgeon, a surgical team, at least one data processor or a combination thereof, the surgeon can lock the image in place.

In an optional fourth calibration step, the controlling surgeon places a calibration target having known dimensions and features into the real-time multidimensional visualization of the target surgical field and triggers the apparatus to calibrate the target surgical field into consistent and useful measurable dimensions.

In a further step, the at least one data processor incorporates at least one real-time, virtual surgical reference indicium or multiple surgical reference indicia including natural patient vertical into the real-time visualization of the target surgical field. The virtual surgical reference indicia including natural patient vertical can be highly patient specific for a particular surgical procedure or can be general for commonplace surgical procedures. For example, in some embodiments suitable for more commonplace procedures, the indicia including natural patient vertical are pre-determined shapes, such as, but not limited to, arcs, lines, circles, ellipses, squares, rectangles, trapezoids, triangles, polygons, irregular volumes, and diamonds including specific information pertaining to the natural patient vertical.

Although in the present exemplary embodiment, the virtual surgical reference indicia including natural patient vertical are incorporated into a real-time visualization after alignment of the still image, in other embodiments, the virtual surgical reference indicia including natural patient vertical are added as early as the capturing of the pre-operative still image. It is within the scope of the present description that the virtual surgical reference indicia including natural patient vertical may be incorporated at any point up until the indicia are needed during a surgical procedure. For example, the virtual surgical reference indicia including natural patient vertical can be added directly on the pre-operative still image instantly after it is captured. The virtual surgical reference indicia including natural patient vertical can be added either with or without the image aligned and locked in place and depends on the particular surgical procedure, needs of the surgeon, or needs of the patient.

It is also within the scope of the present disclosure that a surgeon may input one or more freehand virtual surgical reference indicia including natural patient vertical on a still image or real-time multidimensional visualization. Additionally, it is also contemplated as being within the scope of the present description to utilize pre-operative markings that are placed within the target surgical field on the patient so that the data processor will generate virtual surgical reference indicia including natural patient vertical according to the markings found on the pre-operative data set.

Further still, a surgeon may utilize multiple different virtual surgical reference indicia including one or more natural patient vertical during a single surgical procedure or any subpart thereof. For example, initial reference indicia including natural patient vertical may be replaced by other reference indicia including natural patient vertical at any point during a surgery, or two or more different indicia may be used to represent more complex surgical markings.

It should also be noted that when desired to correspond to a real-time 3D HD visualization of the target surgical field, the real-time virtual surgical reference indicia including natural patient vertical can be generated in 3D as well as in HD, or both, depending on the particular surgical procedure or upon the needs of the surgeon. In some embodiments, either the real-time virtual surgical reference indicia or natural patient vertical can be in 3D and/or HD and vice versa. For example, and not intended to be a limitation, a 3D HD real-time virtual surgical reference indicia can be paired with a 2D standard definition natural patient vertical.

As described above in reference to FIG. 10, once pre-operative patient data still image 1002 has been locked in place over real-time 3D HD visualization 1000 of the target surgical field, the apparatus incorporates at least one real-time, virtual surgical reference indicium including natural patient vertical into the combined aligned pre-operative patient data still image 1002 with real-time 3D HD visualization 1000 of the patient's eye to function as a precise and accurate surgeon controlled reference indicia to facilitate the surgeon's making of an appropriately sized, shaped and positioned capsulorrhexis and subsequent IOL implantation that will assist in producing superior post-surgical results and patient satisfaction.

Exemplary real-time virtual surgical reference indicia suitable for performing capsulorrhexis procedures using the basic apparatus described herein are described in the Applicant's co-pending U.S. application: Ser. No. 12/249,845 entitled "Real-time Surgical Reference Indicium Apparatus and Methods for Surgical Applications," filed Oct. 10, 2008, all of which is fully incorporated herein by reference as if part of this specification.

Figure 11:
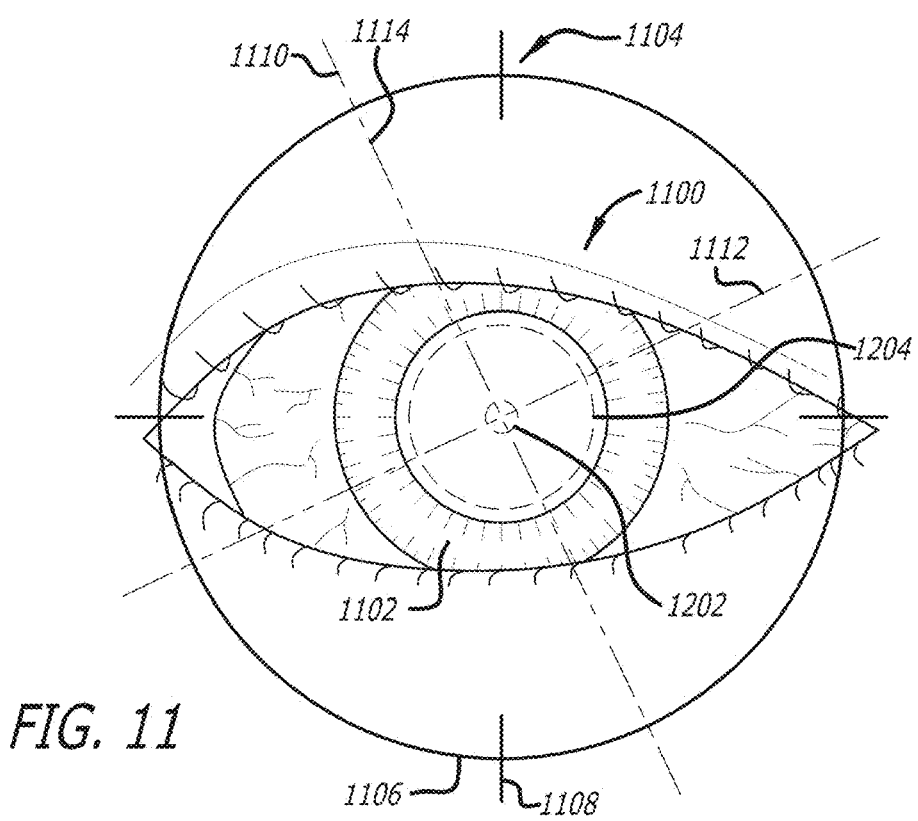
FIG. 11 is a chemically dilated eye with a generated indicium including natural patient vertical and other alignment features.

Virtual surgical reference indicia including natural patient vertical as described herein can be useful in performing an IOL implantation. Since the virtual surgical reference indicia including natural patient vertical described herein can track the true vertical axis of a patient's eye, such an indicia can be particularly useful for IOL implantation. Referring to FIG. 11, eye 1100 is chemically dilated as evidenced by symmetrically dilated iris 1102. In one embodiment, indicium including natural patient vertical 1104 has a substantially circular shape. It should be noted that indicium including natural patient vertical 1104 can have any shape that may be useful for implantation of an IOL. Other shapes that can be useful include, but are not limited to ellipses, squares, rectangles, diamonds, stars, trapezoids and the like. Combinations of shapes may also be useful. Indicium including natural patient vertical 1104 includes compass card 1106. In one embodiment, compass card 1106 can include one or more graduated markings 1108 for orientation reference. Graduated markings 1108, can include information such as, but not limited to, degree markings, limit information, minimum and maximum settings, true patient axis markings and the like.

Further, indicium including natural patient vertical 1104 includes accurate information about the patient's true vertical axis. For example, cross-hatch 1110 can be used to track the true vertical axis of a patient's eye. Cross-hatch 1110 includes horizontal member 1112 and vertical member 1114. It is most common for vertical member 1114 to track the true vertical axis of a patient's eye. It is within the scope of the present disclosure that the natural patient vertical be identified by some means within indicium including natural patient vertical 1104. The identification means does not have to be of the form of cross-hatch 1110, but can be as simple as a straight solid line, a dashed line or the like.

It should be noted that it is within the scope and teachings of the present disclosure that the virtual surgical reference indicia including natural patient vertical can be sized and modified according to the needs of the surgeon. For example, the indicium including natural patient vertical can be sized, rotated and moved horizontally, vertically, and in depth as needed by the surgeon.

Further, the virtual surgical reference indicia including natural patient vertical can be composed of different types of indication markings and can be in HD. For example, without limitation, the markings can be monochromatic or colored, with varying levels of transparency, composed of thin or thick lines, dashed or solid lines, a series of different shapes and the like as is consistent with contemporary digital graphics technology. Further, the graphic presentation can be different within individual indicia to more easily visualize the indicium in different areas or to emphasize specific areas of interest.

Typically, once indicium including natural patient vertical 1104 has been added to a real-time visualization of the target surgical field and is properly aligned with the natural patient vertical, a surgeon can implant an IOL within the capsular sac. It is within the scope of the present description that the IOL can be inserted into the capsular sac prior to the insertion of indicium including natural patient vertical 1104 and subsequently aligned with the indicium. Regardless, the IOL is aligned by the surgeon with natural patient vertical.

Figure 12:
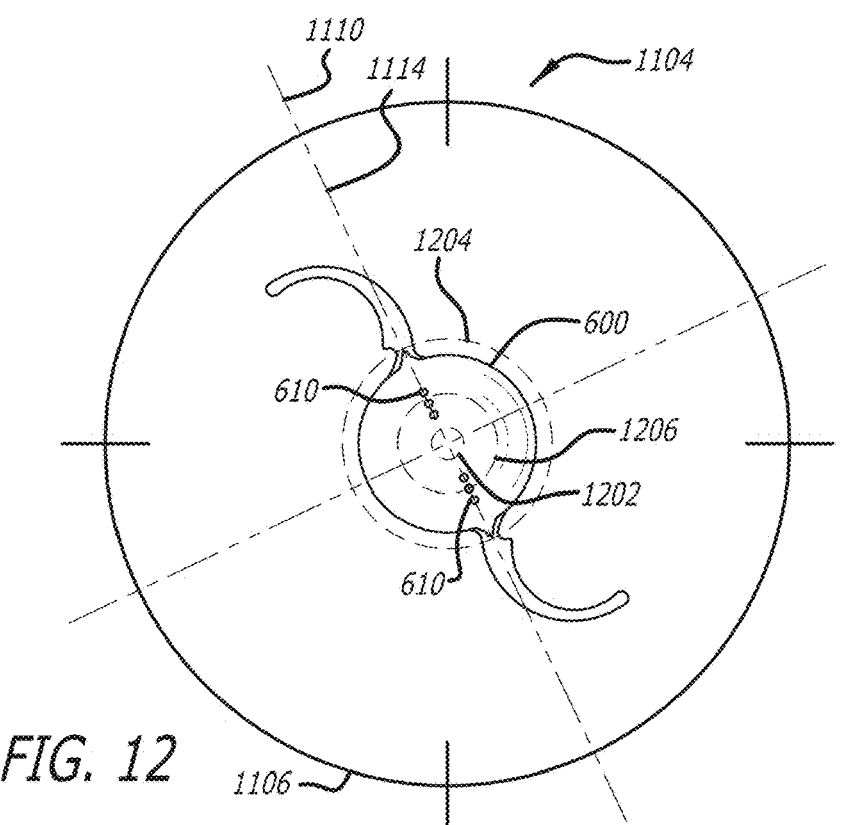
FIG. 12 is an implanted IOL with a generated indicium including natural patient vertical and other alignment features.

Referring to FIG. 12, IOL 600 has been implanted into eye 1100, however, for the sake of clarity, only IOL 600 has been depicted. IOL 600 also includes orientation markings 610,610 which are useful by a surgeon in properly aligning IOL 600 once implanted.

Orientation markings 610, 610 are aligned with vertical member 1114, aligned with natural patient vertical, of cross-hatch 1110, which is aligned with the patient's vertical axis. Once IOL 600 has been properly aligned with natural patient vertical, the indicium is removed and the surgical procedure completed.

A further advantage of the apparatus and methods described herein can be seen in FIG. 12. The virtual surgical reference indicia including natural patient vertical can be custom tailored to a specific IOL shape. For example, shapes can be added to the indicia to improve proper placement of IOL 600 within the capsular bag. For example, center point 1202 can be used to center the focal center of IOL 600 within the proper position in the eye. If center point 1202 is not sufficient to properly center IOL 600, then outline 1204 can be used as a guide to properly position IOL 600. It is within the scope of the present description that the general outline of any IOL can be used to generate outline 1204.

Figure 13:
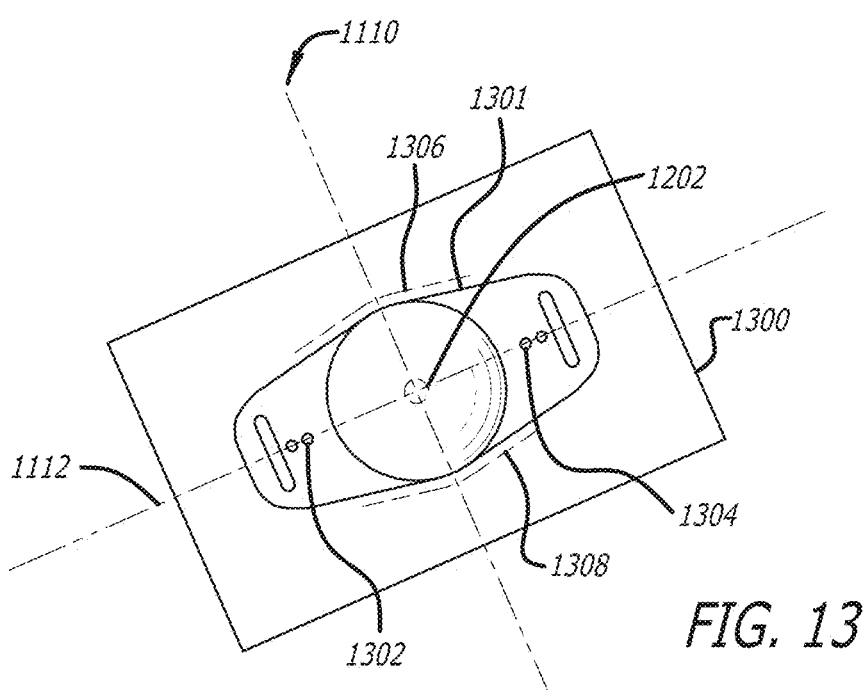
FIG. 13 is another implanted IOL with a generated indicium including natural patient vertical and other alignment features.

A second non-limiting example wherein second virtual surgical indicia including natural patient vertical 1300 has a rectangular shape and has a least a partial outline of an IOL is illustrated in FIG. 13. Phakic IOL 1301 is oriented longitudinally along the steep axis of astigmatism. Alignment marks 1302 and 1304 allow a surgeon to align IOL 1301 with horizontal member 1112 of cross-hatch 1110. To further aid a surgeon, partial outlines 1306 and 1308 guide the surgeon in properly orienting IOL 1301 within the eye concurrently with assuring proper alignment with the natural astigmatic axis of the patient's eye. Although in this embodiment, partial outlines are used, a full outline can be used, but it can be advantageous for a surgeon to only use outlines visible beyond the iris.

Figure 14:
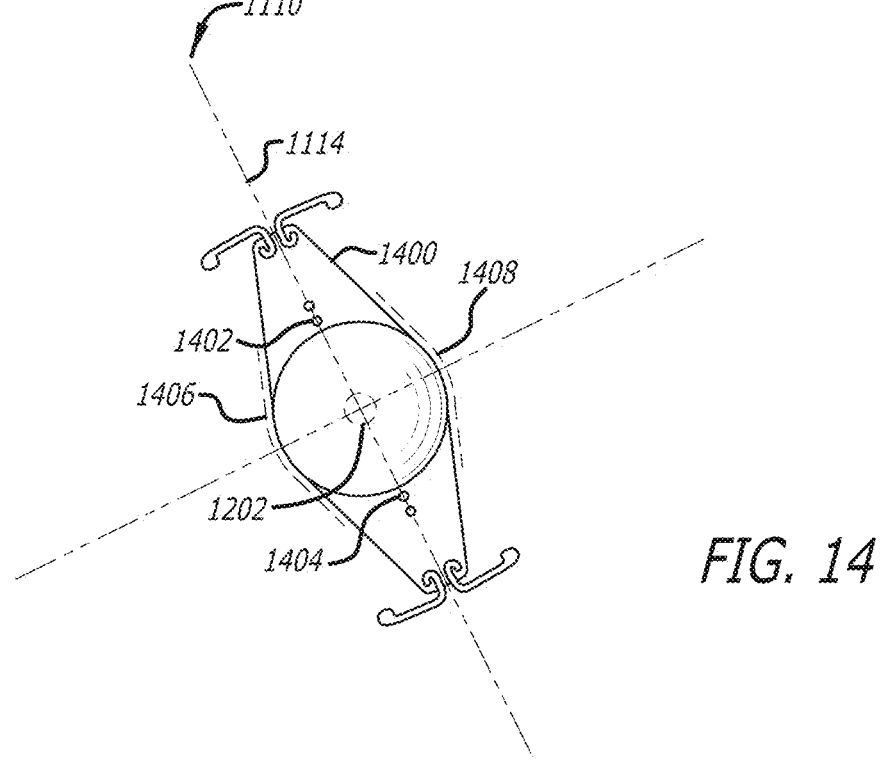
FIG. 14 is still another implanted IOL with a generated indicium including natural patient vertical and other alignment features.

A further non-limiting example wherein virtual surgical indicia including natural patient vertical has a least a partial outline of an IOL, but has no general indicium shape as the previous indicia, is illustrated in FIG. 14. Vaulting IOL 1400 is oriented vertically along the natural patient vertical of an eye. Alignment marks 1402 and 1404 allow a surgeon to align IOL 1400 with vertical member 1114 of cross-hatch 1110. To further aid a surgeon, partial outlines 1406 and 1408 guide the surgeon in properly orienting IOL 1400 within the eye concurrently with assuring proper alignment with natural patient vertical.

Further, outlines 1204, 1306, 1308, 1406 and 1408, for example, can be generated to guide a surgeon in properly centering one or more distinct focal regions of an IOL. Because many modern IOLs can have several distinct focal regions (termed multifocal IOLs), it can be important for a surgeon to properly align these focal regions with respect to the natural patient vertical. For example, focal outline 1206 in FIG. 12 can be useful to a surgeon attempting to center a particular focal region of the IOL. Properly placing an IOL within an eye is a 3D process and the virtual surgical reference indicia including natural patient vertical can aid a surgeon in each of the three dimensional alignments.

A surgeon will find that the apparatus and methods disclosed herein provide many more advantages over existing technology. Firstly, as ocular surgeons are aware, orientation markings commonly associated with IOLs are hard enough to see with the naked eye, let alone having to align them using best guess or manual marking techniques on the ocular tissues. The present disclosure provides apparatus and methods which assist a surgeon in accurately aligning orientation markings on an IOL with the natural patient vertical by providing easy to see real-time virtual surgical indicia including natural patient vertical.

Further, the reference indicium or indicia including natural patient vertical are not affected by the surgical procedure itself. Therefore, they remain as constant references even when the target tissues are subjected to fluids and wiping. More importantly, the indicia including natural patient vertical are precise, accurate and tissue and structure specific, rather than the approximations known in the art. Further, they can be changed, removed, and reinstated as needed to provide an added degree of control and flexibility to the performance of a surgical procedure. For example, a controlling surgeon can chose to vary the transparency or remove a reference indicium including natural patient vertical altogether from a visualization to give a more clear view of underlying tissues or structural features and then reinstate the indicium including natural patient vertical to function as a template or guide for an incision or orientation of an implantable medical device in the target tissue or structure.

Further provided are significant advantages to patient and physician comfort as well as to a surgeon's stamina. This is because the real-time visualizations of the apparatus and methods allow the surgery to take place under ambient or low ambient light conditions without sacrificing complete and accurate visualization of the target surgical field or of the associated reference indicium including natural patient vertical. These capacities can be ideal for a surgeon and surgical team working long hours. Working such long hours under bright lights that generate intense heat in order to visualize the target surgical area, as is commonly the case in many known surgical procedures, can result in previously unavoidable surgeon discomfort and fatigue. Additionally, it is not uncommon for a surgeon to be wearing several layers of clothing along with surgical barriers, including gloves, face barriers, goggles, hats, and overcoats, to name a few, during a given surgical procedure, further contributing to discomfort and fatigue.

As an additional benefit of the described apparatus and methods, the ambient or low ambient lighting conditions that now can be utilized without sacrificing visualization and control also reduce reflected glare and high contrast shadows in the surgical environment that, in the past, could confuse or possibly even overwhelm the vision of the surgeon. Prior to the present description, a related visual limitation in surgery was that a surgeon commonly required surgical team members or students to position themselves out of certain areas in order to reduce shadows that they might cast on the target surgical site. This resulted in limiting their view of the surgery. The present description addresses this problem by reducing shadows and increasing visibility, especially of the target site.

Similarly, it is not uncommon for a surgeon to look away from a target surgical site in order to change or to move equipment, to take a mental break, or to communicate with a surgical team or students. Upon looking back onto the traditional target surgical site, the surgeon would have to wait briefly to allow his eyes to adjust to the normal high intensity lighting, causing delays in the procedure. The present apparatus and methods eliminate this problem under low ambient light conditions.

Even further still, the apparatus and methods described herein allow a surgical team to position themselves in the most appropriate location for the surgery, not necessarily where the shadows dictate. Moreover, the apparatus and methods provide an ideal environment for students to observe a procedure in comfortable ambient to low ambient light conditions, especially when used with multiple screens or with a large display such as a projection screen.

The use of ambient or low ambient light in medical or surgical processes and the resulting reduced heat and complexity in the operating room also adds to the comfort of a surgical patient and enhances the compliance of the patient with the needs of the surgeon. Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. Further, if it is ocular surgery, bright lights that are commonly used to attain better detail in the target surgical field can be very uncomfortable for a patient and can cause the eye to move and twitch. Such scenarios can be problematic for a patient. The present apparatus and methods' low ambient light capabilities can simplify and shorten a medical procedure, provide enhanced patient comfort and compliance, and improve the medical procedure's outcome; all while providing the surgeon with enhanced visual control of the process.

As those skilled in the art will appreciate, these capabilities result from the capacity of the present apparatus and methods to work with light outside of the visible range. Exemplary still images and videos captured at one or more wavelengths of light outside the visible range can be wavelengths of light shorter or longer than wavelengths of visible light. Exemplary wavelengths of light within the scope and teachings of the present invention are those with wavelengths longer that those of visible light, specifically between about 700 nm and about 1400 nm. Exemplary wavelengths that are outside of the wavelengths of normal visible light within the scope of the present invention also include wavelengths of light that are shorter than the wavelengths of visible light. These include wavelengths in the ultraviolet range or "UV," x-rays and gamma rays ranging from about 400 nm or less. A person skilled in the art should be cautious when using wavelengths of light shorter than the visible spectrum because, although such wavelengths of light can be advantageous for certain medical procedures, such wavelengths can be damaging to tissues.

More specifically, exemplary wavelengths longer than those in the visible spectrum can include wavelengths between about 700 nm to about 1000 nm or 1 millimeter. As those skilled in the art also will appreciate, such longer than visible wavelengths are commonly referred to as infrared or "IR" wavelengths and are not visible to the eye. Infrared radiation is commonly known as heat. There are different regions in the infrared portion of the electromagnetic spectrum. Near-infrared corresponds to light with a wavelength between about 700 nm to about 1400 nm. Short infrared corresponds to light with a wavelength between about 1.4 micrometers ($\mu$m) to about 3 $\mu$m. Mid-wavelength infrared corresponds to light with a wavelength between about 3 $\mu$m to about 8 $\mu$m. Long-wavelength infrared corresponds to light with a wavelength between about 8 $\mu$m to about 15 $\mu$m. Far infrared corresponds to light with a wavelength between about 15 $\mu$m to about 1 mm. In one exemplary embodiment, the photosensor can detect any wavelength of light in the infrared region.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An apparatus for stereoscopic guidance of a surgical procedure on an eye, the apparatus comprising:

at least one real-time, multidimensional visualization module configured to record left and right images of the eye, the eye having at least one identifiable visual feature;

at least one display in communication with the multidimensional visualization module;

wherein the at least one real-time, multidimensional visualization module includes an image processor adapted to produce, using the left and right images, at least one real-time stereoscopic multidimensional visualization of the eye on the at least one display;

a foot switch device adapted to signal an increase or a decrease in a viewing depth of a currently displayed view of the at least one real-time stereoscopic multidimensional visualization, in response to user input;

wherein the at least one identifiable visual feature is characterized by a first depth in the at least one real-time stereoscopic multidimensional visualization; and at least one data processor configured to:

i) produce at least one virtual surgical reference indicium characterized by a second depth based on a pre-operative still image of the eye, ii) scroll through different values of the viewing depth of the at least one real-time stereoscopic multidimensional visualization, based on the user input to the foot switch device, and iii) align the at least one virtual surgical reference indicium to the eye in conjunction with the at least one real-time stereoscopic multidimensional visualization of at least a portion of the eye based in part on the viewing depth.

2. The apparatus of claim 1, wherein the at least one data processor is configured to adjust at least one of a color, luminosity, and transparency of the least one real-time stereoscopic multidimensional visualization relative to a target surgical field of view.

3. The apparatus of claim 1, wherein the multidimensional visualization module includes a photosensor.

4. The apparatus of claim 1, wherein the foot switch device is further adapted to activate a second virtual surgical reference indicium to facilitate alignment of an intraocular lens with the second virtual surgical reference indicium.

5. The apparatus of claim 4, wherein the second virtual surgical reference indicium includes one or more of a partial outline of the intraocular lens, a full outline of the intraocular lens, degree markings, limit information, minimum settings, maximum settings, cross-hatch marks, a center point, or combinations thereof.

6. The apparatus of claim 5, wherein the partial outline of the intraocular lens, the full outline of the intraocular lens, or both, vary based on a shape of the intraocular lens of the surgical procedure among multiple potential intraocular lenses for the surgical procedure, each of the multiple potential intraocular lenses including a different shape.

7. The apparatus of claim 1, further comprising a photosensor configured to capture the pre-operative still image of the eye.

8. The apparatus of claim 1, wherein the apparatus is configured such that the pre-operative still image of the eye is captured prior to a cyclorotation of the eye.

9. The apparatus of claim 1, wherein the apparatus is configured such that the pre-operative still image is captured under natural dilation or chemical dilation.

10. The apparatus of claim 1, wherein the at least one real-time stereoscopic multidimensional visualization is three dimensional (3D).

11. The apparatus of claim 1, wherein the at least one real-time stereoscopic multidimensional visualization is high definition (HD).

12. The apparatus of claim 1, wherein the at least one virtual surgical reference indicium is fixed in orientation relative to the at least one identifiable visual feature in the pre-operative still image of the eye.

13. The apparatus of claim 1, wherein the at least one identifiable visual feature comprises at least one structure selected from a group including: vasculature, vascular networks, vascular branching patterns, patterns in an iris, scratches on a cornea, dimples on the cornea, retinal features, a limbus, a pupillary boundary, deformities, voids, blotches, sequestered pigment cells, scars, relatively darker regions, and combinations thereof.

14. The apparatus of claim 1, wherein the left and right images of the eye in the at least one real-time stereoscopic multidimensional visualization are captured by a photosensor of the multidimensional visualization module, and wherein the pre-operative still image of the eye is captured using the photosensor.

15. A method of stereoscopic guidance of a surgical procedure on an eye of a patient, the method comprising:

obtaining a pre-operative still image of the eye;

recording left and right images of the eye, the eye having at least one identifiable visual feature;

producing, using the left and right images, at least one real-time stereoscopic multidimensional visualization of the eye for display on a display device, the at least one identifiable visual feature characterized by a first depth in the at least one real-time stereoscopic multi-dimensional visualization;

producing at least one virtual surgical reference indicium characterized by a second depth using the pre-operative still image;

receiving input from a foot switch device to signal either an increase or a decrease in a viewing depth of a currently displayed view of the at least one real-time stereoscopic multidimensional visualization on the display device; and aligning the at least one virtual surgical reference indicium to the eye in conjunction with the at least one real-time stereoscopic multidimensional visualization of at least a portion of the eye based in part on the viewing depth.

16. The method of claim 15, further comprising adjusting at least one of a color, luminosity, or transparency of the least one real-time stereoscopic multidimensional visualization relative to a target surgical field of view.

17. The method of claim 15, wherein obtaining the pre-operative still image comprises capturing the pre-operative still image while the patient is sitting up and prior to the patient lying down for the surgical procedure.

18. The method of claim 15, wherein obtaining the pre-operative still image comprises capturing the pre-operative still image while the eye is dilated under natural dilation or chemical dilation.

19. The method of claim 15, further comprising receiving second input at the foot switch device to activate a second virtual surgical reference indicium, the second virtual surgical reference indicium selected to facilitate alignment of an intraocular lens with the second virtual surgical reference indicium.

20. The method of claim 19, wherein the second virtual surgical reference indicium includes one or more of a partial outline of the intraocular lens, a full outline of the intraocular lens, degree markings, limit information, minimum settings, maximum settings, cross-hatch marks, a center point, or combinations thereof.

* * * * *